United States Patent [19]

Malek et al.

[11] Patent Number: 5,712,127
[45] Date of Patent: Jan. 27, 1998

US005712127A

[54] SUBTRACTIVE AMPLIFICATION

[75] Inventors: Lawrence T. Malek, Brampton; Roy R. Sooknanan, Toronto, both of Canada

[73] Assignee: Genescape Inc., Ontario, Canada

[21] Appl. No.: 639,763

[22] Filed: Apr. 29, 1996

[51] Int. Cl.$^6$ .............................. C12P 19/34; C12Q 1/68
[52] U.S. Cl. .................. 435/91.21; 435/91.2; 435/91.3; 435/91.5; 435/91.51; 435/6
[58] Field of Search ........................... 435/6, 91.1, 91.2, 435/91.21, 91.3, 91.5, 91.51

[56] References Cited

U.S. PATENT DOCUMENTS

| | | | |
|---|---|---|---|
| 4,683,202 | 7/1987 | Mullis | 435/91 |
| 4,889,818 | 12/1989 | Gelfand et al. | 435/194 |
| 5,130,238 | 7/1992 | Malek et al. | 435/91 |
| 5,409,818 | 4/1995 | Davey et al. | 435/91.2 |
| 5,436,142 | 7/1995 | Wigler et al. | 435/91.2 |
| 5,455,166 | 10/1995 | Walker | 435/91.2 |
| 5,459,055 | 10/1995 | Jendrisak et al. | 435/199 |
| 5,466,586 | 11/1995 | Davey et al. | 435/91.21 |
| 5,503,979 | 4/1996 | Kramer et al. | 435/6 |
| 5,545,522 | 8/1996 | Van Gelder et al. | 435/6 |
| 5,554,517 | 9/1996 | Davey et al. | 435/91.21 |

OTHER PUBLICATIONS

Fahy, et al., "Self-sustained sequence replication (3SR):An Isothermal Transcription-based Amplification System Alternative to PCR", PCR Methods and Applications, pp. 25–33, (1991).

Hubank, et al., "Identifying differences in mRNA expression by representational difference analysis of cDNA", Nucleic Acids Research, vol. 22, No. 25, pp. 5640–5648, (1994).

Kuze, et al., "A new vector and RNase H method for the subtractive hybridization", Nucleic Acids Research, vol. 17, No. 2, pp. 807, (1989).

Lamar, et al., "Y–Encoded, Species–Specific DNA in Mice: Evidence That the Y Chromosome Exists in Two Polymorphic Forms in Inbred Strains", Cell, vol. 171–177, (1984).

Lisitsyn, et al., "Cloning the Differences Between Two Complex Gnomes", Science, pp. 946–951, (1993).

Mullis, et al., "Specific Enzymatic Amplification of DNA In Vitro: The Polymerase Chain Reaction", Cold Spring Harbor Symp. Quant. Biol., vol. 51, pp. 263–273, (1986).

Myers, et al., "Reverse Transcription an dDNA Amplification by a Thermus thermophilus DNA Ploymerase", Biochemistry, vol. 30:31, pp. 7661–7666, (1991).

Rosen, et al., "Subtractive Hybridization: A Technique Isolation of Differentially Expressed Genes", Toxicology Methods, vol. 4, No. 2, pp. 135–147, (1994).

Saiki, "The Design and Optimization of the PCR", Toxicol. Method., vol. 4, pp. 135–147, (1994).

Sambrook, et al., "Dot and Slot Hybridization of RNA", Molecular Cloning: A Laboratory, pp. 7.53–7.55, (1989).

Sooknanan, et al., "Detection and direct sequence identification of BCR–ABL mRNA in PH$^+$ chronic myeloid leukemia", Experimental Hematology, vol. 21, pp. 1719–1724, (1993).

Sooknanan, et al., "Nucleic Acid Sequence–Based Amplification", Molecular Methods for Virus Detection, pp. 261–285 (1995).

Walker, et al., "A Chemiluminescent DNA Probe Test Based on Strand Displacement Amplification", Molecular Methods for virus Detection, pp. 329–249, (1995).

Wieland, et al., "A method for difference cloning: Gene amplification following subtractive hybridization", Proc. Natl. Acad. Sci. USA, vol. 87, pp. 2720–2724, (1990).

Yang, et al., "Cloning Differentially Expressed Genes", Analytical Biochemistry, vol. 237, 109–114, (1996).

Zeng, et al., "Differential cDNA cloning by enzymatic degrading subtraction (EDS)", Nucleic Acids Research, vol., 22, pp. 4381–4285, (1994).

PCR–Select cDNA subtraction kit, Clontechniques, vol. 10, No. 4, pp. 1–5, (1995).

Palazzolo et al. (1990) Gene 88:25–36.

Rothstein et al. (1993) Methods in Enzymology 225:587–610.

Sive and St. John (1988) Nucleic Acids Research 16:10937.

Kreig and Melton (1987) Methods in Enzymology 155:397–415.

Wyatt et al. (1991) BioTechniques 11:764–769.

*Primary Examiner*—W. Gary Jones
*Assistant Examiner*—Amy Atzel
*Attorney, Agent, or Firm*—Wilson Sonsini Goodrich & Rosati

[57] ABSTRACT

A method is provided for preferentially amplifying target RNA relative to non-target RNA in a sample of tester RNA. According to the method, a sample of tester RNA is contacted with driver sequences which are complementary to the non-target RNA under conditions where the driver sequences hybridize to the non-target RNA. A nucleic acid primer is then extended using the target RNA as a template, forming a DNA template complementary to some or all of the target RNA. The DNA template formed using the target RNA as template is then rendered single-stranded to enable the hybridization of the DNA template to a promoter template. The DNA template is then extended using the promoter template to form an extended DNA template comprising a functional double-stranded promoter. Multiple copies of the target RNA sequence can now be transcribed from the extended DNA template through recognition of the contained functional double-stranded promoter by RNA polymerase.

27 Claims, 9 Drawing Sheets

I.

II.

I.

II.

I.

II.

I.

II.

I.

II.

I.

II.

I.

II.

I.

II.

SUBTRACTIVE AMPLIFICATION

FIELD OF THE INVENTION

This invention relates to a method for selectively amplifying target RNA relative to non-target RNA in a sample of tester RNA.

BACKGROUND OF THE INVENTION

Disease is a deviation from the normal functioning of the body's organs or systems. This deviation can arise in a number of ways: by either an abnormal gene being switched on or by a normal gene being switched off; by chromosomal mutations or rearrangements which frequently result in abnormal or missing gene products in congenital conditions; or by the presence of an infectious agent in genetically normal individuals. In some cases, the total complement of mRNA, the products of gene expression, in an abnormal cell will be different from that in a normal cell. In other cases, there may be no apparent difference in the level of gene expression, but the genetic lesion may be a subtle point mutation giving rise to a defective gene product.

Identification of differences in genetic expression or sequence between normal and abnormal cells is a powerful diagnostic and/or prognostic tool. It can also be the first step in understanding a disease by revealing its underlying mechanism. Thus, identification of genetic differences between normal and abnormal cells can provide a clear path to the design of new diagnostic tests, new drugs or gene therapy.

Methods for identifying and isolating sequences present or actively expressed in one cell but diminished or absent in another cell, referred to as "differential screening" and "difference cloning", have been applied to both genomic DNA and mRNA. Difference cloning is based upon subtractive hybridization, a method for isolating "target" sequences from one DNA population, referred to in this application as "tester", by using an excess of sequences from another DNA population, referred to in this application as "driver". One method of subtractive hybridization mixes a restriction endonuclease-digested tester DNA with an excess of randomly sheared driver DNA (Lamar and Palmer 1994). The DNA mixture is denatured, hybridized and ligated into a compatible restriction site in a cloning vector. Only a tester DNA fragment reannealled to its complement would have both of the correct ends required for cloning. Conversely, any tester DNA fragments that anneal to complementary driver DNA fragments would not have both of the required ends. The low yield of cloned target sequences in this method is due primarily to the slow reannealling of dilute tester sequences to their complements. In addition, the enrichment of unique target sequences from a background of sequences common to the driver is limited by the initial excess of driver to tester.

Other methods of subtractive hybridization are directed toward the preparation of subtracted probes for differential screening of cDNA libraries by in situ colony blot hybridization. In differential screening, differentially expressed nucleic acids are not cloned, but are used as hybridization probes to identify and characterize unenriched cDNA clones. One method described by Kuze, et al. (1989) prepares subtracted RNA probes using hybridization to DNA, followed by digestion with RNase H to separate non-hybridized RNA from the hybrid. After the remaining RNA is purified, the subtractive hybridization process is repeated. Hybridization of immobilized DNA using the purified subtracted RNA probe indicates that the subtracted probes can be enriched at least 100 fold. Kuze et al. does not describe a way in which the sequences of the subtracted RNA itself may be cloned or amplified, or suggest a use for the subtracted RNA other than as a hybridization probe.

Some improvements to the subtractive hybridization methods, as applied to difference cloning, involve the use of nucleic acid amplification processes selectively to increase the copy number of a DNA segment having the target sequence. An improvement to subtractive hybridization described by Wieland, et al. (1990) uses the "polymerase chain reaction" (PCR) to increase the concentration of target sequences, and multiple steps of annealing tester DNA to excess driver DNA to further enrich the unique target sequences from a background of sequences common to the driver. In this procedure tester DNA fragments are first prepared for amplification by ligating to a "template" oligonucleotide. A mixture of prepared tester DNA and a 200-fold excess of randomly sheared driver DNA is denatured and reannealled to 90% completion, after which the remaining single-stranded DNA containing target sequences is purified from the double-stranded DNA containing the driver. After three rounds of denaturation, annealing and purification, the remaining tester DNA is then amplified in PCR using primers that anneal to the template sequences. The double-stranded PCR products are then cloned and sequenced. The method gave a 100- to 700-fold enrichment of target sequences.

Another improvement to subtractive hybridization described by Lisitsyn, et al. (1993) is a technique called "representational difference analysis" (RDA). RDA lowers the complexity of both tester and driver genomic DNA by using various restriction endonucleases, e.g. BamHI, BglII and HindIII, to generate fragments of a particular length that can be efficiently amplified in PCR as "representations" of the genome. The tester and driver fragments are ligated to dephosphorylated oligonucleotide adaptors such that an adaptor sequence is ligated to the 5'-end of each strand. The adapted fragments are then amplified in separate PCR reactions using the adaptor as a primer to achieve kinetic enrichment of a population of "amplicons" that are below 1 kb in size. Finally, the tester and driver amplicons is digested with the same restriction endonuclease to remove the original adaptors.

The "difference analysis" step of RDA is based upon the kinetic and subtractive enrichment of the tester amplicons in a second PCR. It begins with ligating different dephosphorylated oligonucleotide adaptors, this time only to the tester amplicons. An excess of driver amplicons are then mixed with the adapted tester fragments, denatured, and allowed to anneal. A portion of the annealed fragments is then treated with a DNA polymerase to allow extension of driver and adapted tester strands using the complementary driver or adapted tester strands as template. The annealed and extended amplicons are then amplified in PCR using the adaptor as a primer. Driver strands annealed to complementary driver strands will not be extended or amplified. Driver strands annealed to complementary adapted tester strands will be extended, but will lack a 5'-terminal adaptor sequence that is necessary to form a template for exponential amplification in PCR. Only the adapted tester strands that anneal to their complementary adapted tester strands and are extended prior to PCR will contain sequences on both 5' and 3' ends to enable exponential amplification.

Following 10 cycles of PCR, a portion of the amplified products is treated with a nuclease to specifically degrade single-stranded nucleic acids. After inactivating the nuclease, a portion of the remaining nucleic acids is further amplified in PCR using the same primer. After 15 to 20 more cycles of PCR, the double-stranded DNA products are digested with the restriction endonuclease, and the process of difference analysis is repeated. After sufficient rounds (typically 3 to 4, for example) of RDA are performed, the double-stranded DNA products are finally cloned and analyzed.

Although RDA was originally developed for genomic DNA, a variation of RDA has been more recently applied to cDNA (Hubank, and Schatz, 1994). Since the cDNA population derived from a typical cell represents only 1–2% of the total genome, kinetic enrichment to reduce complexity should not be necessary for RDA when applied to cDNA. Dephosphorylated oligonucleotide adaptors are ligated to tester and driver cDNA fragments that are generated by digestion of the double-stranded cDNA with a frequently cutting restriction endonuclease, e.g. DpnII. The adapted cDNA fragments are amplified separately by PCR and the resulting amplicons are digested with the same restriction endonuclease to remove the adaptor sequences. The tester cDNA amplicons are then subjected to multiple rounds of RDA as described for genomic DNA.

Despite many successful applications of subtractive hybridization, the various methodologies have been described as "technically difficult, time consuming and often either impractical or unreliable" (Hubank, and Schatz, 1994). One difficulty encountered with subtractive hybridization is the requirement for physical removal of hybridized tester sequences prior to amplification and/or cloning. Another limitation of subtractive hybridization is related to self-reassociation kinetics of complex genomes. Similarly, RDA shares some of the problems common to other subtractive hybridization methods. One is the requirement for self-reannealling of complementary tester sequences to enable amplification. For rare cDNA sequences (less than 1%, for example) this imposes kinetic limitations and requires lengthy hybridizations (of 20 hours, for example). Another limitation of RDA is the amplification of a double-stranded tester DNA that requires the use of an excess (typically 100-fold) of double-stranded driver DNA to compete with the re-annealing of complementary tester DNA strands. A single-stranded tester nucleic acid could more effectively hybridize with a complementary single-stranded driver. DNA. To avoid physical removal of hybridized sequences, RDA requires the covalent activation and inactivation of tester sequences prior to amplification. [For subsequent rounds of RDA, these modifications must be removed with a restriction enzyme, new primers must be ligated and the newly modified tester must be subjected to hybridization with driver and activation/inactivation steps before the next application of PCR.] This multi-step process becomes a serious practical problem with RDA, in that the PCR amplification step is vulnerable to contamination by less enriched amplified products. Anti-contamination procedures cannot be implemented since the amplicons must remain intact and active as a template throughout the various steps of each round of RDA.

Thus, there is a need for a process for the enrichment of nucleic acid sequences which: 1) avoids hybrid removal prior to amplification; 2) does not require concentration-limiting self-annealing of tester nucleic acids; 3) utilizes single-stranded tester and driver nucleic acids; 4) avoids modification of the tester nucleic acids between rounds of subtractive hybridization and amplification; and 5) integrates hybridization, inactivation, and exponential amplification into a process with fewer steps, thus avoiding contamination.

SUMMARY OF THE INVENTION

The method of this invention, called subtractive amplification, represents a novel combination of subtractive hybridization and nucleic acid amplification. Subtractive amplification has the following advantages: 1) it avoids the physical removal of hybridized sequences before amplification; 2) it avoids a concentration-limiting self-annealing of tester nucleic acids in order to activate them for amplification; 3) it improves hybridization efficiency by using single-stranded tester and driver nucleic acids; 4) it avoids modification of the tester nucleic acids after the hybridization step to activate them for amplification; 5) it avoids modification of the tester nucleic acids between rounds of subtractive hybridization and amplification; 6) it allows a simple dilution procedure to prepare the products of one round of subtractive amplification reaction for the next round of subtractive amplification; and 7) it minimizes contamination by integrating multiple rounds of subtractive hybridization and exponential amplification into a process with fewer steps.

This invention relates to a method for preferentially amplifying target RNA relative to non-target RNA in a sample of tester RNA, in which each tester RNA comprises a terminal priming sequence for amplification, and wherein target RNA is either absent or less represented in a mixture of driver nucleic acids the method comprising: 1) a hybridization reaction, wherein the tester sequences are provided in a medium comprising driver sequences under conditions such that driver sequences hybridize with complementary tester sequences, the tester sequence that anneal to driver sequences (non-target RNA) being thereby rendered incapable of functioning as templates for nucleic acid synthesis; 2) a reverse transcription reaction, wherein tester sequences from the hybridization reaction are provided in a medium comprising a first primer and a reverse transcriptase under conditions such that the tester RNA sequences that do not anneal to the driver sequences, (referred to herein as "target RNA"), hybridize to the first primer and provide templates for synthesis of DNA templates by extension of the annealed first primer using the reverse transcriptase, thereby forming RNA:DNA hybrids, the RNA strands of which are degraded; 3) a DNA conversion reaction, wherein DNA templates from the reverse transcription reaction are provided in a medium comprising a DNA polymerase and a promoter template under conditions such that the DNA template hybridizes to the promoter template and are extended using the DNA polymerase, thereby forming DNA templates with functional double-stranded promoters; and 4) a transcription reaction, wherein DNA templates with attached promoters from the DNA conversion reaction are provided in a medium comprising an RNA polymerase under conditions such that the RNA polymerase recognizes the double-stranded promoter and synthesizes from each DNA template copies of the target RNA sequences.

According to one embodiment of the process, the driver nucleic acid sequences are composed of DNA. In one aspect of this embodiment, a portion of the hybridization reaction is added to a degradation reaction medium comprising a ribonuclease that hydrolyzes the RNA of an RNA:DNA hybrid under conditions such that the non-target RNA tester sequences that anneal to the DNA driver sequences are degraded, and a portion of the degradation reaction is added to the reverse transcriptase reaction, hence providing target RNA tester sequences. In another aspect of this embodiment, the hybridization reaction medium further a ribonuclease that hydrolyzes the RNA of an RNA:DNA hybrid under conditions such that the non-target RNA tester sequences that anneal to the DNA driver sequences are degraded. Another aspect of this embodiment relates to the particular ribonucleases that may be used.

According to another embodiment, in each step of the process all or a portion of one reaction may be added to a subsequent reaction. In one aspect of this embodiment, a portion of the hybridization reaction is added to the reverse transcription reaction, hence providing target RNA tester sequences. In another aspect of this embodiment, a portion of the reverse transcriptase reaction is added to the DNA conversion reaction, hence providing DNA templates. In another aspect of this embodiment, a portion of the DNA conversion reaction is added to the transcription reaction, hence providing DNA templates with functional double-stranded promoters.

According to another embodiment of the process, a portion of the reverse transcription reaction is added to a degradation reaction medium comprising a ribonuclease that hydrolyzes the RNA of an RNA:DNA hybrid under conditions such that the target RNA tester sequences forming a hybrid with the DNA templates are degraded, and a portion of the degradation reaction is added to the DNA conversion reaction, hence providing DNA templates.

According to another embodiment of the process, a portion of the reverse transcription reaction is added to a denaturation reaction under conditions such that the DNA templates are separated from the target RNA tester sequences of the RNA:DNA hybrid, and a portion of the denaturation reaction is added to the DNA conversion reaction, hence providing DNA templates.

According to another embodiment of the process, the reverse transcription reaction medium further comprises a ribonuclease that hydrolyzes the RNA of an RNA:DNA hybrid under conditions such that the target RNA tester sequences forming a hybrid with the DNA template are degraded.

According to another embodiment of the process, a portion of the reverse transcription reaction is added to a DNA amplification reaction medium comprising the first primer, a second primer and a DNA polymerase under conditions such that the DNA template hybridizes to the second primer and is extended using the DNA polymerase to form a double-stranded DNA and the strands of the double-stranded DNA are separated, upon which a cycle ensues wherein: i) the first primer and the second primer each hybridize to their complementary DNA strands; ii) each primer is then extended using the DNA polymerase to form a double-stranded DNA; and iii) the complementary DNA strands of the double-stranded DNA are separated, and thereafter a portion of the DNA amplification reaction is added to the DNA conversion reaction, hence providing DNA templates.

In one aspect of this embodiment, the DNA amplification reaction is the polymerase chain reaction, wherein the complementary DNA strands of the double-stranded DNA are separated by adjusting the reaction conditions to cause denaturation. In another aspect of this embodiment, the DNA amplification reaction is by strand displacement amplification, wherein the reaction medium further comprises a restriction endonuclease under conditions that the restriction endonuclease nicks the primers of the double-stranded DNA and the complementary DNA strands of the double-stranded DNA are separated by the DNA polymerase extending the nicked primers to displace the complementary DNA strands.

According to another embodiment of the process, the DNA conversion reaction medium further comprises a first primer, and the promoter template therein further comprises a second primer under conditions such that the DNA template hybridizes to the second primer and is extended using the DNA polymerase to form a double-stranded DNA, upon which a cycle ensues wherein: i) the complementary DNA strands of the double-stranded DNA are separated; ii) the first primer and the second primer each hybridize to their complementary DNA strands; and iii) each primer is then extended using the DNA polymerase to form a double-stranded DNA, thereby forming DNA templates with functional double-stranded promoters.

In one aspect of this embodiment, the complementary DNA strands of the double-stranded DNA are separated by adjusting the reaction conditions to cause denaturation. In another aspect of this embodiment, the reaction medium further comprises a restriction endonuclease under conditions that the restriction endonuclease nicks the primers of the double-stranded DNA and the complementary DNA strands of the double-stranded DNA are separated by the DNA polymerase extending the nicked primers to displace the complementary DNA strands.

According to another embodiment of the process, the reverse transcription, DNA conversion and transcription reactions together comprise an RNA amplification reaction, wherein target tester RNA sequences are provided in a medium comprising a first primer, a promoter template, a reverse transcriptase, a DNA polymerase and an RNA polymerase under conditions such that the target tester RNA sequences hybridize to the first primer and provide templates for synthesis of DNA templates by extension of the annealed first primer using the reverse transcriptase, thereby forming RNA:DNA hybrids, the RNA strands of which are degraded; the DNA templates hybridize to the promoter template and are extended using the DNA polymerase, thereby forming DNA templates each with a functional double-stranded promoter; and the RNA polymerase recognizes each double-stranded promoter and synthesizes from the DNA templates copies of the target RNA sequences.

In one aspect of this embodiment, the DNA polymerase is reverse transcriptase. In another aspect of this embodiment, the RNA amplification reaction medium further comprises a ribonuclease that hydrolyzes the RNA of an RNA:DNA hybrid under conditions such that the RNA tester sequences forming hybrids with the DNA templates are degraded. In another aspect of this embodiment, a portion of the hybridization reaction comprising the target tester RNA sequences that do not anneal to the driver sequences is added to the RNA amplification reaction, hence providing target tester RNA sequences. In another aspect of this embodiment, target RNA sequences from one round of the RNA amplification reaction provide target tester RNA sequences in a subsequent round of the RNA amplification reaction. In another aspect of this embodiment, a portion of the RNA amplification reaction comprising target RNA sequences from one round of the process is added to the hybridization reaction of a subsequent round of the process, hence providing tester RNA sequences.

According to another embodiment of the process, target RNA sequences from one round of the process provide tester RNA sequences in a subsequent round of the process. In one aspect of this embodiment, a portion of the transcription reaction comprising target RNA sequences from one round of the process is added to the hybridization reaction of a subsequent round of the process, hence providing tester RNA sequences.

According to another embodiment of the process, a mixture of RNA comprising target RNA sequences and each comprising terminal priming sequences are added to the hybridization reaction, hence providing tester RNA sequences.

According to another embodiment of the process, the hybridization reaction further comprises an RNA polymerase, and to which is added a mixture of DNA templates each with a functional double-stranded promoter, under conditions such that the RNA polymerase recognizes each double-stranded promoter and synthesizes from the DNA templates copies of a mixture of RNA comprising target RNA sequences and each comprising terminal priming sequences, hence providing tester RNA sequences. In one aspect of this embodiment, terminal sequences and a double-stranded promoter are appended to DNA templates from which tester RNA sequences are synthesized using an RNA polymerase.

According to another embodiment, a final round of the subtractive amplification process comprises: 1) a hybridization reaction; 2) a reverse transcription reaction; 3) a DNA duplexing reaction, wherein DNA templates from the reverse transcription reaction are provided in a medium comprising a DNA polymerase and a second primer under conditions such that the DNA templates hybridize to the second primer and provide templates for synthesis of double-stranded DNA templates by extension of the annealed second primer using the DNA polymerase.

According to one aspect of this embodiment, the DNA duplexing reaction is performed within a DNA amplification reaction wherein the DNA duplexing reaction medium further comprises a first primer under conditions such that the second primer hybridizes to the DNA templates and is extended using the DNA polymerase to form double-stranded DNA templates, upon which a cycle ensues wherein: i) the complementary DNA strands of each double-stranded DNA template is separated; ii) the first primer and the second primer each hybridizes to their complementary DNA template strands; and iii) each primer is then extended using the DNA polymerase to form double-stranded DNA templates.

According to another aspect of this embodiment, the double-stranded DNA templates of the duplexing reaction are characterized by cloning and sequencing. In one aspect of this embodiment, the characterized sequences are used to make hybridization probes or amplification primers. In another aspect of this embodiment, the characterized sequences are used to identify or characterize a useful nucleic acid sequence. In another aspect of this embodiment, the cloned DNA templates are used for the preparation of tester RNA sequences or driver nucleic acid sequences.

BRIEF DESCRIPTION OF THE DRAWINGS

In drawings which illustrate embodiments of the invention.

DETAILED DESCRIPTION OF THE PREFERRED EMBODIMENTS

Figure 1:
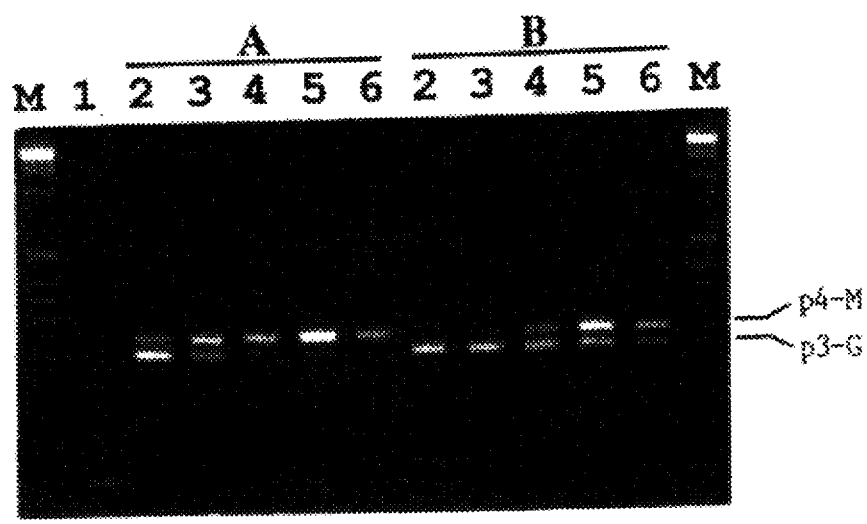
FIG. 1 shows agarose gel electrophoretic analysis of the products of subtractive amplification using PCR, where (I) is a photograph of the products detected by ethidium bromide staining, and (II) is an autoradiogram of the products detected by blot hybridization to radiolabeled oligonucleotide probes.
Figure 1:
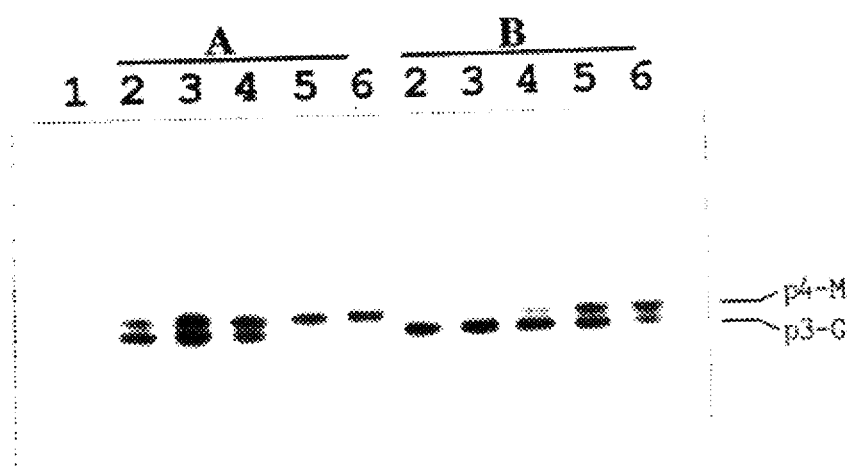

This invention relates to a method for preferentially amplifying target RNA relative to non-target RNA in a sample of tester RNA. The tester RNA and driver nucleic acid sequences are prepared from nucleic acids isolated from at least two different populations of cells. The tester RNA and driver nucleic acid sequences are of opposite senses; for example, the tester RNA may have the same sense as the mRNA of a cell (+sense), while the driver nucleic acid would have the sense complementary to that of the mRNA (−sense). The target RNA sequences are a subset of the tester RNA sequences. Those sequences that would be complementary to the target RNA sequences are either absent or less represented among the population of driver nucleic acid sequences. Target RNA sequences can be operationally defined as those of the tester RNA sequences that do not anneal to the driver nucleic acid sequences. Conversely, non-target RNA is operationally defined as those tester RNA sequences that do anneal to the driver nucleic acid sequences.

This process can be applied to the discovery of target RNA sequences encoding proteins, such as cytokines, hormones, growth factors or receptors, by using tester RNA sequences prepared from induced cells and driver nucleic acid sequences prepared from uninduced control cells. A kit for this process comprising a number of receptacles containing the reagents required for the process may be contemplated. The application of this process results in useful products. For example, the enriched target nucleic acid sequences when amplified by the process of this invention or the proteins encoded by these target nucleic acid sequences. The process can be used to find target RNA sequences representing infectious agents, for example viruses or bacteria, by using tester RNA sequences prepared from infected samples and driver nucleic acid sequences from uninfected controls. The process can also be used to isolate target nucleic acid sequences responsible for a disease, disorder, or abnormal physical state, for example to find causes for human health problems, e.g. inherited disorders, or cancer, by using nucleic acids from diseased test cells and normal control cells. The use of the process of this invention to diagnose may also be contemplated. The unique nucleic acid sequences identified by this process could be used for diagnostic purposes or for gene therapy or as targets for the discovery of pharmaceuticals. The proteins that are encoded by the sequences could be used for preparing appropriate immunodiagnostic reagents. The encoded proteins could also be used therapeutically either on their own as biopharmaceuticals or as targets for the discovery of pharmaceuticals.

For a general application where the target RNA sequences represent uniquely or more abundantly expressed gene sequences, the tester RNA sequences and driver nucleic acid sequences are both derived from the mRNA of their respective cell populations. In order to utilize the mRNA for the preparation of tester RNA sequences and driver nucleic acid sequences, a complementary DNA or cDNA is generally prepared from each mRNA. Various methods for the preparation and cloning of cDNA from natural RNA are known in the art. Thereby methods for preparing cDNA from natural RNA are not limited to those described hereinafter.

First, an RNA-specific primer may be hybridized to the natural RNA and extended to synthesize a cDNA using reverse transcriptase, thereby forming an RNA-DNA hybrid. The RNA-specific primer typically comprises a 3' terminal oligo(dT) sequence that hybridizes to a 3'-terminal polyadenylated sequence that is present in most eukaryotic mRNAs. The RNA-specific primer may further comprise a mixture of sequences of the general formula oligo(dT)VN 3', to avoid synthesis of cDNA from the polyadenylated sequence. Alternatively, a different type of RNA-specific primer may be used for synthesis of cDNA from RNA without using a 3'-terminal polyadenylated sequence. This later type of RNA-specific primer may comprise a mixture of short 3'-terminal oligonucleotide sequences of random composition, or a single arbitrary sequence that hybridizes to the RNA under conditions of low stringency. The RNA-specific sequence may further comprise a recognition site for a restriction endonuclease to enable directional cloning of the cDNA in a plasmid or phage vector.

Second, a cDNA-specific primer may be hybridized to the cDNA and extended to synthesize a double-stranded cDNA using a DNA polymerase. Some methods of second strand cDNA synthesis call for the removal of the RNA strand that is hybridized to the cDNA before hybridization of the cDNA-specific primer. This can be accomplished by thermal or chemical denaturation or by chemical or enzymatic hydrolysis of the RNA strand. The cDNA-specific primer may comprise a mixture of short 3'-terminal oligonucleotide sequences of random composition, or a single arbitrary sequence that hybridizes to the cDNA under conditions of low stringency. Alternatively, the 3' terminus of the cDNA may anneal to another sequence of the same cDNA to form a self-priming hairpin loop. Other methods of second strand cDNA synthesis do not require the removal of the RNA strand, but rather partially hydrolyze the RNA strand with RNase H to provide oligoribonucleotide primers hybridized to the cDNA that are extended using a DNA polymerase to form a double-stranded cDNA.

Finally, the double-stranded cDNA may be subjected to a replication process. Some methods involve the ligation of the double-stranded cDNA into a plasmid or phage vector to allow for the generation of libraries and the cloning of individual sequences. Before ligation into cloning vectors, the double-stranded cDNA is generally first prepared by ligating to oligonucleotide linkers or adapters to each of its ends. Other methods of cDNA replication involve nucleic acid amplification processes, such as PCR, in which the double-stranded cDNA is added to a reaction comprising the RNA-specific primer and the cDNA-specific primer.

Although tester RNA sequences and driver nucleic acid sequences are derived from different populations of cells, it is preferable to use the same method to prepare cDNA from the RNA from each cell population. The cDNA synthesized from each cell population is then specifically adapted for generating either tester RNA sequences or driver nucleic acid sequences.

Each of the tester RNA sequences comprise terminal priming sequences that enable the hybridization of primers for purposes of DNA polymerization, hence amplification. The first primer hybridizes to the tester RNA sequences at their 3'-terminal priming sequences and is extended with a DNA polymerase (reverse transcriptase) to form DNA templates. The DNA templates hybridize at their 3' terminal priming sequences to the promoter template and are extended with a DNA polymerase to form a double-stranded promoter attached to each DNA template. Additionally, if the promoter template further comprises the second primer, then the DNA polymerase further extends the second primer to form a double-stranded DNA comprising the DNA template and a double-stranded promoter. The priming sequences are of sufficient length and base composition to enable hybridization with their respective primers under the conditions suitable for the DNA polymerases.

The tester RNA sequences can be prepared by a variety of methods, not limited to those described hereinafter. Tester RNA sequences can be preferably generated by in vitro transcription of DNA templates that are each joined to a double-stranded promoter and are complementary to tester RNA sequences such that an RNA polymerase recognizes the double-stranded promoter and synthesizes copies of the tester RNA sequences from the DNA templates. Prior to such in vitro transcription, the priming sequences may be added to the DNA templates by ligation of primers, annealed with their complementary adapters, to the ends of the DNA templates that are generated using restriction endonucleases (Lisitsyn, et al. 1993). The restriction endonucleases preferably generate a 5'-terminal single-stranded sequence of typically four nucleotides in length. The 5'-terminal sequence used to ligate the first primer and its adapter is preferably different from the 5'-terminal sequence used to ligate the second primer and its adapter. For example, the restriction endonuclease Sau3AI may be used to generate 5'-terminal single-stranded GATC sequences to which is ligated the first primer annealed to its adapter, whereas the restriction endonuclease MluI may be used to generate 5'-terminal single-stranded CGCG sequences to which is ligated the promoter template comprising the second primer annealed to its adapter. The DNA templates from which the tester RNA sequences are generated may be obtained from either a mixture of cDNA synthesized directly from mRNA by reverse transcription or a library of cDNA cloned in a plasmid or phage vector.

The driver nucleic acid sequences may be composed of any nucleic acid that when hybridized to the tester RNA sequence will impair the capability of the tester RNA sequences to serve as a template for a DNA polymerase, that is a reverse transcriptase. The driver nucleic acid may block the RNA template from a DNA polymerase that is incapable of displacing it during extension of the first primer. Alternatively, the hybridization of driver nucleic acid to the tester RNA may provide a substrate for enzymatic RNA hydrolysis. As such, any method for preparing the driver nucleic acid sequences should provide a strand of nucleic acid that would be complementary to the tester RNA sequences.

In the preferred embodiment of the process, the driver nucleic acid sequences are composed of DNA. The driver DNA sequences are single-stranded in the hybridization reaction, but may originate from a double-stranded DNA or RNA-DNA hybrid. Methods for the preparation of single-stranded driver DNA must ensure that the sense that is complementary to the tester RNA is provided in the hybridization reaction. A single-stranded DNA may be obtained from a double-stranded DNA by thermal denaturation or by selective degradation of one strand by a 3' or 5' exonuclease, for example. A single-stranded driver DNA may be obtained from phage particles that package a single-stranded genomic DNA, M13 for example, or from phage particles that contain a single-stranded plasmid, a phagemid for example, with phage replication and packaging sequences, an f1 origin of replication, for example. Alternatively, the single-stranded driver DNA may be obtained from a cDNA synthesized from an mRNA.

Certain embodiments of this invention involve the use of nucleic acid amplification methods to increase the copy number of target sequences. Amplification methods can be used for either diagnostic or discovery applications. For diagnostic purposes, primers are designed for specificity to a particular nucleic acid sequence that may be present in the sample. The nucleic acid sequence is generally already known to the user. For discovery purposes, the nucleic acid sequence is unknown. Application of the amplification process requires adaptations of the nucleic acids to provide particular sequences that are specific to the primers. Many nucleic acid amplification processes known in the art are signal amplification methods, which merely alter the oligonucleotide sequences that are initially present in the reaction in response to the added target sequence. Hence, signal amplification processes are not suitable for discovery of new sequences. There are only three known amplification processes that actually generate target-specific sequence information that is not initially present in the reaction, and are useful for sequence discovery.

U.S. Pat. No. 4,683,202 describes an amplification process, known as the "polymerase chain reaction" (PCR), which involves the use of two primers and a DNA polymerase. In general, PCR involves treating the sample suspected of containing a target DNA sequence with oligonucleotide primers such that a primer extension product is synthesized by a DNA polymerase. The primer extension product DNA strand is separated from the template strand in the preferred embodiment using heat denaturation. Both the original template and the primer extension product then serve as templates in the next and subsequent cycles of extension, resulting approximately in the doubling of the number of target DNA sequences in the sample at the end of each cycle. Consequently, multiple cycles result in the quasi-exponential amplification of the target nucleic acid sequence. Optimal practice of the PCR requires the use of a thermocycler capable of rapid changes of temperature and of a DNA polymerase, such as Taq polymerase (U.S. Pat. No. 4,683,195) that resists the denaturation caused by repeated exposure to temperatures above 90° C. required to separate the DNA strands.

U.S. Pat. No. 5,455,166 of Becton Dickinson Co. describes another nucleic acid amplification process, referred to as "strand displacement amplification" (SDA), with exponential reaction kinetics that takes place at a relatively constant temperature throughout and without serial addition of reagents. An SDA reaction contains two enzymes, a restriction endonuclease and a DNA polymerase, two primers, each of which have a central restriction site, and an α-thioated deoxynucleoside triphoshate. Its 8-step cyclic process repeats the following steps for each strand of the DNA product: (1) the first primer anneals to a first single-stranded DNA product; (2) the DNA polymerase uses the first primer and first single-stranded DNA product for bidirectional synthesis of an α-thioated double-stranded DNA product; (3) the restriction endonuclease nicks the primer of the α-thioated double-stranded DNA product; and (4) the DNA polymerase extends the nicked primer to synthesize a new strand of the double-stranded DNA product while simultaneously displacing a second single-stranded DNA product. The second single-stranded DNA product, which is complementary to the first single-stranded DNA product, then anneals with the second primer and is used to make the original first single-stranded DNA product by repeating the first four steps to complete the cycle.

U.S. Pat. No. 5,409,818 of Cangene Corporation describes an amplification process which involves the use of a first primer, a second primer which has a promoter, an RNA polymerase, a DNA polymerase (a reverse transcriptase) and a ribonuclease (RNase H) that specifically degrades the RNA strand of an RNA-DNA hybrid. The cyclic process takes place at a relatively constant temperature throughout and without serial addition of reagents, wherein the first primer hybridizes to the RNA product, reverse transcriptase uses the RNA product as template to synthesize a DNA product by extension of the first primer, RNase H degrades the RNA of the resulting RNA-DNA hybrid, the second primer with the promoter hybridizes to the DNA product, reverse transcriptase uses the second primer as template to synthesize a double-stranded promoter by extension of the DNA product, and RNA polymerase uses the promoter and DNA product to transcribe multiple copies of the same RNA product. In the most commonly practiced embodiment of this invention, in a process referred to as NASBA, the ribonuclease from the reverse transcriptase is supplemented with a cellular RNase H. U.S. Pat. No. 5,130, 238 of Cangene Corporation describes an enhanced nucleic acid amplification process that is similar to that described in U.S. Pat. No. 5,409,818, but is enhanced by addition to the reaction mixture of an alkylated sulfoxide (for example, dimethyl sulfoxide) and BSA.

The process of the present invention, subtractive amplification, can be described as a four-step process. It will be understood that the numbering of steps in the process is of purely heuristic value in defining the relative order of molecular events but not the actual number of reactions that may be performed. The reactions of two or more steps may be combined into a single reaction medium and performed as one step. Also additional reactions may be interpolated between steps. Similarly, each reaction is performed in a medium, as designated, and under conditions that enable the reaction. More than one reaction may be performed in the same medium under the same or different conditions.

The first step of the process comprises a hybridization reaction wherein the tester RNA sequences are provided in a medium comprising driver nucleic acid sequences under conditions such that driver sequences hybridize with complementary tester sequences, the tester sequences that hybridize to driver sequences (non-target RNA) being thereby rendered incapable of functioning as templates for nucleic acid synthesis. In the preferred embodiment, a mixture of RNA comprising target RNA sequences, with each RNA comprising terminal priming sequences, is added to the hybridization reaction, hence providing tester RNA sequences.

The hybridization reaction is performed under appropriate conditions of pH, ionic strength and temperature to ensure that the driver hybridizes effectively and specifically to complementary sequences in the mixture of tester RNA sequences. Hybridization conditions may be selected among those that are described in the art, not limited to the following references cited herein: (Sambrook, et al. 1989; Lisitsyn, et al., 1993; Hubank and Schatz, 1994; and Rosen, et al., 1994). In addition, certain agents or solvents may be included in the hybridization reaction that increase specificity, facilitate hybridization at a lower temperature, or increase the hybridization kinetics. It is preferable that the hybridization conditions are compatible with any enzymes that are used subsequently to or concommitantly with the hybridization reaction. It is contemplated that the hybridization products may be purified from any incompatible components of the hybridization reaction before subsequent steps of the process.

The hybridization reaction may further comprise such agents that may promote the degradation or inactivation of the non-target RNA tester sequences that hybridize to the driver nucleic acid sequences. This degradation or inactivation would supplement the inhibition by hybridized driver nucleic acid sequences of strand displacement during extension of the first primer with the reverse transcriptase. In the preferred embodiment, the hybridization reaction medium further comprises a ribonuclease, an RNase H, that hydrolyzes the RNA of an RNA:DNA hybrid under conditions such that the non-target RNA tester sequences that anneal to the driver DNA sequences are degraded. The RNase H which could be used in this embodiment may be any enzyme capable of hydrolyzing any RNA that is annealed to any complementary DNA, and not capable of hydrolyzing single or double-stranded RNA or any DNA. Preparations comprising the RNase H should be relatively free of contaminating agents with DNase or RNase activities. Additionally, the RNase H that is used in this embodiment should be preferably capable of remaining stable and active under the hybridization conditions so that the non-target RNA tester sequences may be hydrolyzed during the hybridization reaction. Preparations of such ribonucleases that are stable at elevated temperatures and uses thereof are taught in U.S. Pat. No. 5,459,055 of Epicentre Technologies Corporation. A thermostable bacterial RNase H that is suitable for this purpose may be selected from *Thermus thermophilus*, *Thermus flavus* or any other thermophilic bacteria known in the art.

Alternatively, in another embodiment, a portion of the hybridization reaction may be added to a degradation reaction medium comprising a ribonuclease, an RNase H, that hydrolyzes the RNA of an RNA:DNA hybrid under conditions such that the non-target RNA tester sequences that hybridize to the driver DNA sequences are degraded. The RNase H which could be used in this embodiment should have the same activities and qualities as set forth in the aforementioned embodiment, with the single exception of remaining stable and active under the hybridization conditions. Since the hydrolysis of the tester RNA may be performed at conditions other than those used for hydridization, the RNase H that is suitable for this purpose may be selected from *Escherischia coli* or any other bacteria known in the art.

The second step of the process comprises a reverse transcription reaction, wherein tester sequences from the hybridization reaction are provided in a medium comprising a first primer and a reverse transcriptase under conditions such that the tester RNA sequences that do not anneal to the driver nucleic acid sequences (i.e., target RNA) hybridize to the first primer and provide templates for synthesis of DNA templates by extension of the annealed first primer using the reverse transcriptase, thereby forming RNA:DNA hybrids, the RNA strands of which are degraded. In the preferred embodiment of the process, the RNA tester sequences are provided by adding a portion of the hybridization or degradation reactions to the reverse transcription reaction. In one embodiment of this process the reverse transcription reaction comprises part of an RNA amplification method, for example, NASBA.

The first primer is an oligodeoxyribonucleotide comprising a 3'-terminal sequence which is complementary to the 3'-terminal priming sequence of the tester RNA sequences. The first primer is of a particular length and base composition to allow specific and efficient synthesis of DNA templates from the tester RNA sequences under the conditions of the reverse transcription reaction. The first primer should also have a 3'-terminal sequence that minimizes annealing to itself or another primer in the reaction such that a primer would be extended using itself or another primer as template in a DNA or RNA amplification reaction, hence producing what is described in the art as "primer-dimers". It is contemplated that the first primer may be composed in part of nucleotides other than deoxyribonucleotides provided that a first primer of such composition may still function as template for DNA and RNA synthesis.

The reverse transcriptase which is used in this invention may be any enzyme capable of synthesizing DNA from an oligonucleotide primer and an RNA template. In addition to RNA-directed DNA polymerase, this enzyme may further comprise activities for DNA-directed DNA polymerase and RNase H. Preparations comprising the reverse transcriptase should be relatively free of contaminating agents with DNase or RNase activities. Additionally, the reverse transcriptase should be capable of remaining stable and active under the reverse transcription reaction conditions. In the preferred embodiment, a retrovital DNA polymerase is used. For example, in subtractive amplification using PCR, the reverse transcriptase from Maloney murine leukemia virus (MMLV) is used. Subtractive amplification with NASBA uses the reverse transcriptase from avian myeloblastosis virus (AMV) in the RNA amplification reaction. Certain DNA-directed DNA polymerases known in the art having RNA-directed DNA polymerase activity under certain reaction conditions may also be used in this invention. For example, a method is described for performing RT-PCR using the thermostable DNA polymerase from *Thermus thermophilus* in the presence of manganese (II) salts to relax the natural specificity for DNA templates and allowing DNA synthesis also from RNA templates (Myers, and Gelfans, 1991). If the reverse transcriptase reaction is to be followed immediately by PCR, then degradation of the tester RNA template is unnecessary. It is further contemplated that other enzymes and conditions that are used to commence PCR from an RNA template may be employed in the reverse transcriptase reaction of this process.

The reverse transcription reaction comprises the necessary concentrations of cofactors and nucleoside triphosphates for DNA synthesis using the particular reverse transcriptase. The reverse transcription reaction is performed under the conditions of pH, ionic strength and temperature that are appropriate to the enzyme which is used. Such reaction conditions are known to those skilled in the art.

The third step of the process comprises a DNA conversion reaction, wherein DNA templates from the reverse transcription reaction are provided in a medium comprising a DNA polymerase and a promoter template under conditions such that the DNA templates hybridize to the promoter template and are extended using the DNA polymerase, thereby forming DNA templates with functional double-stranded promoters. In the preferred embodiment, the DNA templates are provided by adding a portion of the reverse transcriptase reaction to the DNA conversion reaction.

The promoter template is an oligodeoxyribonucleotide comprising a 3'-terminal sequence which is complementary to the 3'-terminal priming sequence of the DNA templates. The promoter template is of a particular length and base composition to allow specific and efficient synthesis of double-stranded promoters by extension of the DNA templates under the conditions of the DNA conversion reaction. The promoter template contains the plus (+) sense sequence of a promoter and transcription initiation site. This sequence, when used as a template in the DNA conversion reaction, contains sufficient information to allow specific and efficient binding of a RNA polymerase and initiation of transcription at the desired site. In the preferred embodiment, the promoter and initiation sequence are specific for the RNA polymerase from the bacteriophage T7. The plus (+) sense sequence of the T7 RNA polymerase promoter typically comprises the 17-nucleotide sequence 5'-TAATACGACTCACTATA-3' (SEQ. ID. NO. 1), which is immediately followed by a purine-rich initiation site sequence, typically 5'-GGGAGA-3'. In addition, the promoter template contains a short 5'-terminal sequence of preferably five nucleotides that precedes the promoter, which has been shown in the art to increase the efficiency of transcription (Fahy et. al. 1989). In the preferred embodiment, the 5'-terminal sequence of the promoter template is 5'-AATTCTAATACGACTCACTATAGGGAGA-3' (SEQ. ID. NO. 2). It is understood by those skilled in the art that some changes may be made in the promoter and initiation sequences specified herein and still achieve sufficient levels of transcription.

In some embodiments, the promoter template further comprises a second primer of a particular length and base composition to allow specific and efficient synthesis of a double-stranded DNA by extension of the second primer. The second primer should also have a 3'-terminal sequence that minimizes annealing to itself or another primer in the reaction such that a primer would be extended using itself or another primer as template in a DNA or RNA amplification reaction, hence producing what is descibed in the art as "primer-dimers". It is contemplated that the second primer may be composed in part of nucleotides other than deoxyribonucleotides provided that a primer of such composition may still function as template for DNA and RNA synthesis.

The DNA polymerase which is used in this invention may be any enzyme capable of synthesizing DNA from an oligodeoxyribonucleotide primer and a DNA template. Preparations comprising the DNA polymerase should be relatively free of contaminating agents with DNase or RNase activities. Additionally, the DNA polymerase should be capable of remaining stable and active under the DNA conversion reaction conditions. The particular DNA polymerase that is used will depend on whether the DNA conversion reaction is part of an RNA or DNA amplification reaction, as set forth hereinafter.

The DNA conversion reaction comprises the necessary concentrations of cofactors and nucleoside triphosphates for DNA synthesis using the particular DNA polymerase. The DNA conversion reaction is performed under the conditions of pH, ionic strength and temperature that are appropriate to the enzyme which is used. Such reaction conditions are known to those skilled in the art.

In one embodiment of this process, the DNA conversion reaction comprises part of an RNA amplification reaction, for example NASBA. In this embodiment, the DNA templates are provided by the reverse transcription step of the RNA amplification reaction and the DNA polymerase is preferably the same enzyme as the reverse transcriptase. Subtractive amplification with NASBA uses the reverse transcriptase from avian myeloblastosis virus (AMV) in the RNA amplification reaction, though another retroviral polymerase could be used. An RNA amplification process, such as NASBA, does not require the promoter template to function also as a primer. It is even preferable that the promoter template used in this embodiment is actually blocked to avoid the formation of primer-dimers from any primer extension following self-annealing. The various methods in the art for blocking a primer generally include substitution of the terminal 3'-OH with another chemical moiety.

In another embodiment of this process, the DNA conversion reaction is performed within a DNA amplification reaction. In this embodiment, the DNA conversion reaction medium further comprises a first primer, and the promoter template therein further comprises a second primer under conditions such that the second primer hybridizes to the DNA templates and is extended using the DNA polymerase to form double-stranded DNA templates, upon which a cycle ensues wherein: i) the complementary DNA strands of each double-stranded DNA template are separated; ii) the first primer and the second primer each hybridize to their complementary DNA strands; and iii) the primers are then extended using the DNA polymerase to form double-stranded DNA templates, thereby forming DNA templates with functional double-stranded promoters. In effect, the DNA conversion reaction is replaced with a modified DNA amplification reaction.

In another embodiment, a portion of the reverse transcription reaction is first added to a DNA amplification reaction medium comprising the first primer, a second primer and a DNA polymerase under conditions such that the second primer hybridizes to the DNA templates and is extended using the DNA polymerase to form double-stranded DNA templates, and the complementary strands of each double-stranded DNA template are separated, upon which a cycle ensues wherein: i) the first primer and the second primer each hybridizes to their complementary DNA strands; ii) the primers are then extended using the DNA polymerase to form double-stranded DNA templates; and iii) the complementary DNA strands of each double-stranded DNA template are separated; and thereafter a portion of the DNA amplification reaction is added to the DNA conversion reaction, hence providing DNA templates.

The DNA amplification reaction may be the polymerase chain reaction ("PCR"), wherein the complementary DNA strands of the double-stranded DNA are separated by adjusting the reaction conditions to cause denaturation. The DNA polymerase that is used for DNA conversion and amplification in PCR should be preferably capable of remaining stable under the denaturation and hybridization conditions of PCR. Such DNA polymerases may be prepared from a thermophilic bacteria, such as Thermus aquaticus, Thermus thermophilus or Pyroccocus furigenes. The reaction medium comprises the necessary concentrations of cofactors and nucleoside triphosphates for DNA synthesis using the particular DNA polymerase. PCR is also performed under the conditions of pH, ionic strength and temperature that are appropriate to the enzyme which is used. Each step of strand separation, primer hybridization and primer extension are controlled using a thermal cycling device, whereby each reaction temperature is maintained for a fixed duration, and each cycle of three steps may be repeated a predetermined number of times. PCR reaction conditions suitable to the practice of this invention are known to those skilled in the art (Mullis, et al., 1996; Saiki 1989.

Alternatively, the DNA amplification reaction may be strand displacement amplification, wherein the reaction medium further comprises a restriction endonuclease and the first and second primers further comprise recognition sites for the restriction endonuclease under conditions such that the restriction endonuclease nicks the primers of the double-stranded DNA and the complementary DNA strands of the double-stranded DNA are separated by the DNA polymerase extending the nicked primers to displace the complementary DNA strands. The restriction endonuclease is one which can cut the unmodified primers but cannot cut the modified DNA extension product. The choice of DNA polymerase and restriction endonuclease depends on the temperature which is maintained throughout the SDA reaction. At a relatively moderate temperature, for example 41° C., the Klenow fragment of E. coli DNA polymerase I and the restriction endonuclease Hinc II may be used. Optimal practice of SDA generally uses a more elevated reaction temperature. The SDA reaction comprises the necessary concentrations of cofactors and nucleoside triphosphates for DNA synthesis using the particular DNA polymerase. In particular the SDA reaction contains an α-thioated nucleoside triphosphate, such as (α-thiol)dATP, replacing the natural nucleoside triphosphate, such as dATP. The SDA reaction is performed under the conditions of pH, ionic strength and temperature that are appropriate to the enzymes which are used. SDA reaction conditions suitable to the practice of this invention are known to those skilled in the art (Walker, et al. 1995)

The fourth step of the process comprises a transcription reaction, wherein DNA templates with attached promoters from the DNA conversion reaction are provided in a medium comprising an RNA polymerase under conditions such that the RNA polymerase recognizes the double-stranded promoter and synthesizes copies of the target RNA sequences from the DNA template. In the preferred embodiment, the DNA templates with functional double-stranded promoters are provided by adding a portion of the DNA conversion reaction to the transcription reaction. In one embodiment of this process the transcription reaction comprises part of an RNA amplification method, for example, NASBA.

The RNA polymerase which is used in this invention may be any enzyme capable of binding to a particular DNA sequence called a promoter and specifically initiating RNA synthesis at a defined initiation site within close proximity to the promoter. Preparations comprising the DNA polymerase should be relatively free of contaminating agents with DNase or RNase activities. In addition the RNA polymerase should be capable of synthesizing several copies of RNA per functional copy of DNA template in a reasonable period of time. In the preferred embodiment, the bacteriophage T7 RNA polymerase is used. In addition other bacteriophage RNA polymerases, such as phage T3, phage φII, Salmonella phage sp6, or Pseudomonas phage gh-1, may be used. It is understood by those skilled in the art that the use of alternative RNA polymerases will require changes to the sequence of the promoter template according to the specificity of the particular RNA polymerase.

The transcription reaction comprises the necessary concentrations of cofactors and nucleoside triphosphates for RNA synthesis using the particular RNA polymerase. The transcription reaction is performed under the conditions of pH, ionic strength and temperature that are appropriate to the enzyme which is used. Such reaction conditions are known to those skilled in the art.

In one embodiment of the process, the reverse transcription, DNA conversion and transcription reactions together comprise an RNA amplification reaction, wherein tester RNA sequences are provided in a medium comprising a first primer, a promoter template, a reverse transcriptase, a DNA polymerase and an RNA polymerase under conditions such that the tester RNA sequences hybridize to the first primer and provide templates for synthesis of DNA templates by extension of the annealed first primer using the reverse transcriptase, thereby forming RNA:DNA hybrids, the RNA strands of which are degraded; the DNA templates hybridize to the promoter template and are extended using the DNA polymerase, thereby forming DNA templates each with a functional double-stranded promoter; and the RNA polymerase recognizes each double-stranded promoter and synthesizes from the DNA templates copies of the target RNA sequences. The DNA polymerase of the RNA amplification process may be a reverse transcriptase.

In the preferred embodiment, the RNA amplification process is cyclic, wherein the target RNA sequences from one round of the RNA amplification reaction may provide in the same reaction medium tester RNA sequences for a subsequent round of RNA amplification. The RNA amplification reaction comprises the necessary concentrations of cofactors and nucleoside triphosphates for RNA and DNA synthesis using the particular RNA and DNA polymerases described herein. The RNA amplification reaction is performed under the conditions of pH, ionic strength and temperature that are appropriate to the enzymes which are used. In the preferred embodiment, in a process commonly referred to as NASBA, the RNA amplification reaction medium further comprises a ribonuclease, an RNase H, that hydrolyzes the RNA of an RNA:DNA hybrid under conditions such that the RNA tester sequences forming hybrids with the DNA templates are degraded. NASBA reaction conditions suitable to the practice of this invention are known to those skilled in the art (Sooknanan et. al., 1995). In the preferred embodiment, the tester RNA sequences are provided by adding a portion of the hybridization reaction comprising the tester RNA sequences that do not anneal to the driver sequences to the RNA amplification reaction.

For the purpose of further enrichment of target RNA sequences from a mixture of tester RNA sequences that did not effectively anneal to the driver nucleic acid sequences during hybridization, the process may be repeated using the target RNA sequences generated from one round of the process to provide the tester RNA sequences in a subsequent, preferably the next, round of the process. In the preferred embodiment, tester RNA sequences are provided by adding a portion of the transcription reaction comprising target RNA sequences from one round of the process to the hybridization reaction of a subsequent round of the process. For the embodiment of the process where the reverse transcription, DNA conversion and transcription reactions together comprise an RNA amplification reaction, the tester RNA sequences are provided by adding a portion of the RNA amplification reaction comprising target RNA sequences from one round of the process to the hybridization reaction of a subsequent round of the process.

Since the target RNA from one round of the subtractive amplification process can be used as tester RNA for a subsequent or the next round of the process, the initial step of the process becomes arbitrary, though the relative order of the four steps of the process is maintained. In the preferred embodiment of the process involving RNA amplification, the steps of the process have the following order: 1) the hybridization reaction; and an RNA amplification reaction comprising 2) the reverse transcription reaction; 3) the DNA conversion reaction; and 4) the transcription reaction. In the preferred embodiment of the process involving DNA amplification, the steps of the process have the following order: 1) the transcription reaction; 2) the hybridization reaction; 3) the reverse transcription reaction; and 4) a DNA amplification reaction comprising the DNA conversion reaction. In this embodiment, the hybridization reaction may further comprise an RNA polymerase, effectively combining the transcription and hybridization reactions. A mixture of DNA templates each with a functional double-stranded promoter is added to this combined transcription- hybridization reaction, under initial conditions such that the RNA polymerase recognizes each double-stranded promoter and synthesizes from the DNA templates copies of a mixture of RNA comprising target RNA sequences and each comprising terminal priming sequences, hence providing tester RNA sequences. Thereafter, the conditions are changed such that driver sequences hybridize with complementary tester sequences, the tester sequences that anneal to driver sequences being thereby rendered incapable of functioning as templates for nucleic acid synthesis.

It is further contemplated that a cyclic subtractive amplification process could be performed within a single homogeneous reaction, wherein the target RNA sequences from one round of the subtractive amplification may provide in the same reaction medium tester RNA sequences for a subsequent round of subtractive amplification. In this homogenous subtractive amplification reaction, the tester RNA sequences are provided in a medium comprising driver nucleic acid sequences, a first primer, a promoter template, a reverse transcriptase and an RNA polymerase under conditions such that driver sequences hybridize with complementary tester sequences, the tester sequences that anneal to driver sequences being thereby rendered incapable of functioning as templates for nucleic acid synthesis, the tester RNA sequences that do not anneal to the driver sequences hybridize to the first primer and provide templates for synthesis of DNA templates by extension of the annealed first primer using the reverse transcriptase, thereby forming RNA:DNA hybrids, the RNA strands of which are degraded, the DNA templates hybridize to the promoter template and are extended using the DNA polymerase, thereby forming DNA templates with functional double-stranded promoters, and the RNA polymerase recognizes the double-stranded promoter and synthesizes from each DNA template copies of the target RNA sequences. Thereafter, target RNA sequences from one round of subtractive amplification in the same reaction medium tester RNA sequences for a subsequent round of subtractive amplification. The driver nucleic acid sequences may be composed of DNA and the reaction medium may further comprise an RNase H, which would degrade tester RNA sequences that anneal to the driver DNA sequences or form a hybrid with the DNA templates.

It may be desirable, for purposes including cloning of the DNA products, to end the subtractive amplification process with the synthesis of double-stranded DNA templates. In this embodiment, the final round of the subtractive amplification process comprises: 1) a hybridization reaction, wherein the tester sequences are provided in a medium comprising driver sequences under conditions such that driver sequences hybridize with complementary tester sequences, the tester sequences that anneal to driver sequences being thereby rendered incapable of functioning as templates for nucleic acid synthesis; 2) a reverse transcription reaction, wherein tester sequences from the hybridization reaction are provided in a medium comprising a first primer and a reverse transcriptase under conditions such that the tester RNA sequences that do not anneal to the driver sequences hybridize to the first primer and provide templates for synthesis of DNA templates by extension of the annealed first primer using the reverse transcriptase, thereby forming RNA:DNA hybrids, the RNA strands of which are degraded; 3) a DNA duplexing reaction, wherein DNA templates from the reverse transcription reaction are provided in a medium comprising a DNA polymerase and a second primer under conditions such that the DNA templates hybridize to the second primer and provide templates for synthesis of double-stranded DNA templates by extension of the annealed second primer using the DNA polymerase.

The DNA duplexing reaction may be performed within a DNA amplification reaction, wherein the DNA duplexing reaction medium further comprises a first primer under conditions such that the second primer hybridizes to the DNA templates and is extended using the DNA polymerase to form double-stranded DNA templates, upon which a cycle ensues wherein: i) the complementary DNA strands of each double-stranded DNA template are separated; ii) the first primer and the second primer hybridize to their complementary DNA strands; and iii) the primers are then extended using the DNA polymerase to form double-stranded DNA templates.

The first primer that is used in the DNA amplification reactions and the DNA duplexing reactions described herein should be functionally equivalent to the first primer used in the reverse transcriptase reaction but may not necessarily be identical. It is contemplated that additional nucleotides or chemical moieties may be present on one or the other primer.

The double-stranded DNA templates of the duplexing reaction may be characterized by cloning and sequencing. The cloned DNA templates may be utilized as hybridization probes. The probes could take the form of double-stranded plasmid DNA, single-stranded phage or phagemid DNA, or single-stranded RNA transcripts. Alternatively, the characterized sequences may be used in the design of hybridization probes or amplification primers. In this manner, the characterized sequences may be used to identify or characterize a useful nucleic acid sequence. Additionally, the cloned DNA templates could be utilized for the preparation of tester RNA sequences by in vitro transcription, or for the preparation of

21 driver nucleic acid sequences by methods described herein. These tester RNA sequences and driver nucleic acid sequences may be further utilized in the practice of subtractive amplification using tester or driver sequences that are derived from still another cell population.

EXAMPLE 1

Preparation of driver DNA sequences

Cellular RNA was prepared from KG1 cells using standard methods, and cDNA clones encoding the G-CSF receptor (G-CSFR) and the thrombopoeitin receptor (c-mpl) were amplified from the RNA preparation by RT-PCR using primers specific for the G-CSFR and c-mpl sequences, as set forth in Table 1. [Oligonucleotide primers and probes were synthesized on an Applied Biosystems instrument (Model 392-28) (Foster City, Calif.) and were purified by polyacrylamide gel electrophoresis.] Two PCR primers (SEQ. ID. NOs. 3 and 4) were used to amplify a 915-bp fragment of the G-CSFR cDNA sequence (from 241 to 1155 of Genbank Accession No. M59818 M38025) and create cloning sites for NsiI and HindIII. Four PCR primers (SEQ. ID. NOs. 5, 6, 7 and 8) were used to amplify 870- and 568-bp fragments of the c-mpl cDNA sequence (from 76 to 946 and 904 to 1471 of Genbank Accession No. M90103) and create cloning sites for NsiI and HindIII. The two c-mpl cDNA fragments were joined into a single 1414-bp fragment using an overlapping NheI site in the natural cDNA sequence. The PCR products for G-CSFR and c-mpl were digested with NsiI and HindIII and ligated into the PstI and HindIII sites of pT7T319u (Pharmacia). The resulting plasmids, pT7T3-G and pT7T3-M, were then used to prepare single-stranded driver DNA sequences for G-CSFR and c-mpl, respectively. Phagemid DNA of recombinants pT7T3-G and pT7T3-M were isolated according to the procedure supplied with the M13K07 helper phage (New England Biolabs). Each phagemid DNA was purified after SDS-lysis of the phage supernatant and extraction with phenol/chloroform, and quantified at $A_{260\ nm}$.

EXAMPLE 2

Preparation of tester RNA sequences

Specialized vectors were constructed for the cloning of cDNA and the preparation of tester RNA libraries. One of these, pCAT, was constructed by annealing and ligating together four synthetic oligonucleotides, as set forth in Table 2 (SEQ. ID. NOs. 9, 10. 11 and 12) to form a 108-bp fragment, which was ligated into the EcoRI and PstI sites of pUC19 (Pharmacia). A second vector, pCATman, was constructed by annealing and ligating together three synthetic oligonucleotides, as set forth in Table II (SEQ. ID. NOs. 12, 13 and 14) to form a 88-bp fragment, which was ligated into the EcoRI and NheI sites of pCAT. These vectors could be used for in vitro transcription with T7 RNA polymerase to generate RNA that can be amplified using Primer 1 (P1) (SEQ. ID. NO. 11) and Primer 2 (P2) (SEQ. ID. NO. 12).

The vectors pCAT and pCATman were used in the construction of plasmids for the preparation of tester RNA sequences from cDNA subclones of G-CSFR and c-mpl. A 140-bp fragment of G-CSFR cDNA was prepared from the PCR products of the primers identified by SEQ. ID. NOs. 3 and 4, by digestion with StuI, blunt-end ligation of the phosphorylated linker 5' pCTAGCTAG 3', and digestion with PstI and NheI. The sequence of the 144-bp PstI-NheI fragment of G-CSFR cDNA is shown in SEQ. ID. NO. 15

22

(from nucleotides 37 through 168) and in SEQ. ID. NO. 16 (from nucleotides 29 through 168). Similarly, a 144-bp fragment of c-mpl cDNA was prepared from the PCR products of the primers identified by SEQ. ID. NOs. 5 and 6, by digestion with PstI and NheI. The sequence of the 169-bp PstI-NheI fragment of c-mpl cDNA is shown in SEQ. ID. NO. 17 (from nucleotides 37 through 197) and in SEQ. ID. NO. 18 (from nucleotides 29 through 197). The two PstI-NheI fragments were then ligated into the PstI and XbaI sites of pCAT. The resulting plasmids, p3-G and p4-M, were then used to prepare tester RNA sequences by in vitro transcription.

A standard transcription reaction contained 50 mM Tris (pH 8.5), 50 mM KCl, 8 mM $MgCl_2$, 1.5 mM ATP, 1.5 mM GTP, 1.5 mM, CTP, 1.5 mM UTP, 10 mM DTT, 500 ng plasmid DNA, 25 units ribonuclease inhibitor and 60 units T7 RNA polymerase in a final volume of 25 μL. Plasmid DNA from recombinants p3-G and p4-M were first digested with Hind III restriction endonuclease according to the supplier (New England Biolabs) prior to transcription. The components of each transcription reaction were assembled at room temperature and then incubated at 37° C. for 1 hour. Following transcription, 1 unit RQ DNase I was added to each reaction tube and incubation at 37° C. was continued for another 15 minutes. The reaction mixtures were desalted using Bio-gel P6 (BioRad) and the amount of each transcript quantified at $A_{260}$ nm.

The vector pCATman was used for cloning the entire cDNA fragments from the PCR products of Example 1. The 930-bp NsiI-HindIII fragment of G-CSFR cDNA was ligated into the MluI and HindIII sites of pCATman using the oligonucleotide adapter 5' CGCGTGCA 3' to join the MluI and NsiI ends, to make the plasmid p5-G. Similarly, the 1414-bp NsiI-HindIII fragment of c-mpl was ligated into the MluI and HindIII sites of pCATman to make the plasmid p6-M.

EXAMPLE 3

Selective enrichment of a specific nucleic acid sequence after one round of Subtractive Amplification using RT-PCR Single-stranded driver DNA was prepared from the pT7T3-M phagemid according to Example 1, and tester RNAs were prepared from p3-G and p4-M according to Example 2. A standard hybridization reaction contained 40 mM Tris-HCl (pH 8.0), 10 mM $MgCl_2$, 100 mM NaCl, 1mM dithiothreitol (DTT), 1 unit thermostable ribonuclease H (Hybridasea™; Epicentre Technologies), 0.8 pmol ($5×10^{11}$ molecules) single-stranded driver DNA and a tester RNA sample in a final volume of 40 μL. Single-stranded phagemid DNA from pT7T3-M was used as the driver DNA. Various tester RNA mixtures were prepared, with the concentration of p4-M RNA kept constant at 0.19 pmol ($10^8$ molecules) and the concentration of p3-G increased from 0.016 amol ($10^4$ molecules) to 0.16 pmol ($10^8$ molecules)in 10-fold increments (set B). As a control, pT7T3-M driver DNA was not added to a second set of identical hybridization reactions (set A). The components of the hybridization reactions were assembled at room temperature, heated at 75° C. for 2 minutes and then incubated at 65° C. for at least 60 minutes.

Meanwhile, the reagents for nucleic acid amplification using RT-PCR were prepared. Each standard RT-PCR reaction comprised a cDNA synthesis step followed by PCR amplification. The standard cDNA synthesis reaction contained 10 mM Tris-HCl (pH 8.3), 50 mM KCl, 6 mM MgCl$_2$, 1 mM dATP, 1 mM dGTP, 1 mM dCTP, 1 mM TTP, 33 nM Primer 2 and 50 units Maloney murine leukemia virus reverse transcriptase (M-MuLV RT) (Bethesda Research Labs.) in a final volume of 30 µL. In addition, each cDNA synthesis reaction contained a 4-µL aliquot of the nucleic acid from a hybridization reaction or just H$_2$O as a control.

Except for a 2-µL aliquot containing M-MuLV RT, the remaining cDNA synthesis reaction components and nucleic acid sample or H$_2$O were mixed at room temperature, heated at 65° C. for 2 minutes and placed in a 40° C.-water bath. After allowing the reactions to equilibrate at 40° C. for 2 minutes, a 2-µL aliquot containing the M-MLV RT was added to each reaction tube and incubation at 40° C. continued for a further 30 minutes. Next, the tubes were transferred to a thermal-cycler (MiniCyCler™; MJ Research) where they were heated at 99° C. for 5 minutes and then held at 85° C., during which time, a 70-µL aliquot of a PCR-mixture containing 10 mM Tris-HCl (pH 8.3), 50 mM KCl, 0.2 µM Primer 1, 0.2 µM Primer 2 and 1.5 units Taq polymerase (BMC) was added to each reaction tube. PCR amplification was initiated with the following profile: 94° C. for 1 minute, followed by 40 cycles of 94° C. for 40 seconds, 55° C. for 40 seconds and 72° C. for 30 seconds, and finally, 72° C. for 15 minutes.

The amplification products contained in a 5-µL aliquot of each amplification reaction were analysed by agarose gel electrophoresis and Southern blot hybridization (Sambrook, et al. 1989). The Southern blot membrane was hybridized with [5'-$^{32}$P] oligonucleotide probes specific to either p3-G amplicons (SEQ. ID. NO. 19) or p4-M amplicons (SEQ. ID. NO. 20).

The amplified products contained in those reactions to which no pT7T3-M driver DNA was added simply represented co-amplification of the different ratios of p3-G and p4-M RNA transcripts contained in the various mixtures. The p4-M amplicon was visible in all of the reactions (FIG. 1; Lanes A2–6), whereas the p3-G amplicon was only seen in those reactions where the p4-M RNA concentration was no higher than 1000× that of p3-G (Lanes A2–5).

However, when similar RNA mixtures were subjected to the subtraction process using pT7T3-M driver DNA, p4-M amplicons were no longer visible in the reaction that contained similar amounts of p3-G and p4-M transcripts at the start (Lane B2), and only gradually became apparent as the amount of the input p3-G RNA was decreasing (Lanes B3–6). More dramatic, however, was the relative increase in the levels of p3-G amplicons in the various mixtures (Lanes B2–6) including the reaction where essentially no p3-G amplicon was seen in the absence of driver DNA (Lanes A6 vs B6). Infact, in the latter reaction, the relative amounts of the p4-M and p3-G amplicons appeared to be the same after one round of subtractive amplification. Neither p3-G nor p4-M sequences were seen in the reaction where water was added instead of a nucleic acid sample (Lane 1). These results clearly demonstrated significant enrichment of the p3-G sequence following the inactivation of p4-M RNA by its complementary pT7T3-M driver DNA.

In FIG. 1-I and 1-II, the following lanes contain the following materials:
1—no added template
2—10$^8$ p4-M and 10$^8$ p3-G RNA molecules
3—10$^8$ p4-M and 10$^7$ p3-G RNA molecules
4—10$^8$ p4-M and 10$^6$ p3-G RNA molecules
5—10$^8$ p4-M and 10$^5$ p3-G RNA molecules
6—10$^8$ p4-M and 10$^4$ p3-G RNA molecules A—minus driver DNA
B—plus pT7T3-M driver DNA

EXAMPLE 4

Selective enrichment of a specific nucleic acid sequence after two rounds of Subtractive Amplification using RT-PCR The amplified products of a first-round subtractive amplification reaction corresponding to lane B6 of FIG. 1 in Example 3 were serially diluted in 100-fold increments. Because RNA is required to facilitate the subtractive amplification process and since PCR generates only DNA, the PCR amplicons must be first transcribed in order to provide tester RNA for the second-round of subtractive amplification. Thus, a transcription reaction was coupled to the standard hybridization reaction. A standard coupled transcription-hybridization reaction contained 40 mM Tris-HCl (pH 7.5), 50 mM KCl, 15 mM MgCl$_2$, 1.5 mM ATP, 1.5 mM GTP, 1.5 mM CTP, 1.5 mM UTP, 5 mM DTT, 60 units T7 RNA polymerase, 1 unit thermostable RNase H and 0.8 pmol driver DNA in a final volume of 25 µL. In addition, each reaction contained 2.5 µL of either the 10$^{-4}$ or 10$^{-6}$ dilution of the above mentioned first-round reaction or H$_2$O as a control. As an additional control, no driver DNA was added to an identical 10$^{-6}$ dilution of the reaction. The driver DNA used in this example was pT7T3-M phagemid DNA prepared according to Example 1. The reactions were incubated at 40° C. for 30 minutes and then at 65° C. for 60 minutes, after which the reaction tubes were transferred back to 40° C. and 2 minutes. Thereafter, 1 unit of RQ DNase I (Promega) was added to each tube, and incubation at 40° C. was continued for an additional 30 minutes.

Meanwhile, standard RT-PCR amplification reactions were prepared following the teaching of Example 3, using 2-µL aliquots of the coupled transcription-hybridization reactions as tester RNA. The amplification reactions and subsequent detection of the amplified materials were performed according to the teaching of Example 3.

Figure 2:
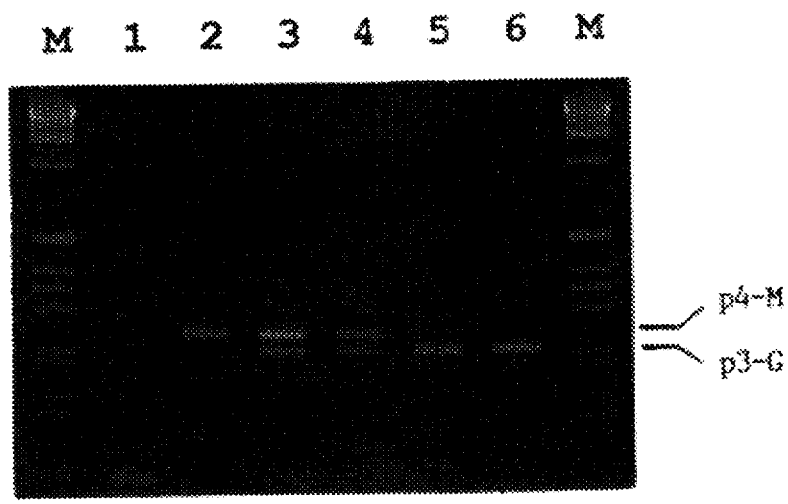
FIG. 2 shows agarose gel electrophoretic analysis of the products of the first and second rounds of subtractive amplification using PCR, where (I) is a photograph of the products detected by ethidium bromide staining, and (II) is an autoradiogram of the products detected by blot hybridization to radiolabeled oligonucleotide probes.
Figure 2:

The results showed no significant difference in the amounts of p3-G and p4-M amplicons upon re-amplification of the first-round reaction product without further subtraction with driver DNA (FIG. 2-I and -II; Lanes 3 vs 4). However, following second-subtraction, the p3-G sequence was predominantly amplified in both dilutions of the said first-round reaction sample (FIG. 2-I, -II; Lanes 5–6). In fact, p4-M amplicons were no longer visible in the re-amplified second-round samples based on the ethidium bromide stained agarose gel (FIG. 2-I; Lanes 5–6). Thus, two rounds of subtractive amplification appeared to have worked well for the selective enrichment of a unique nucleic acid sequence using RT-PCR.

In FIG. 2-I and 2-II, the following lanes contain the following materials:
1—no added template
2—10$^8$ p4-M and 10$^4$ p3-G RNA molecules minus driver DNA
3—10$^8$ p4-M and 10$^4$ p3-G RNA molecules plus driver DNA
4—10$^{-4}$ dilution of #3 minus driver DNA
5—10$^{-4}$ dilution of #3 plus driver DNA
6—10$^{-6}$ dilution of #3 plus driver DNA

EXAMPLE 5

Selective enrichment of a specific nucleic acid sequence after one round of Subtractive Amplification using NASBA Single-stranded driver DNA was prepared from the pT7T3-G phagemid according to Example 1, and tester RNAs were prepared from p3-G and p4-M according to Example 2. Standard hybridization reactions were prepared following the teaching of Example 3, using pT7T3-G as phagemid. In this example, various tester RNA mixtures were prepared, with the concentration of p3-G RNA kept constant at 0.16 fmol ($10^8$ molecules) and the concentration of p4-M RNA increased from 0.019 amol ($10^4$ molecules) to 0.19 fmol ($10^8$ molecules) in 10-fold increments (set B). As a control, pT7T3-G driver DNA was not added to one set of comparable hybridization reactions (set A). The hybridization reactions were incubated following the teaching of Example 3.

Meanwhile, the reagents for the RNA amplification (NASBA) reactions were prepared. Each standard NASBA reaction contained 40 mM Tris-HCl (pH 8.5), 12 mM $MgCl_2$, 50 mM KCl, 10 mM DTT, 2 mM ATP, 2 mM CTP, 2 mM GTP, 2 mM UTP, 1 mM dATP, 1 mM dCTP, 1 mM dGTP, 1 mM TTP, 15% (v/v) dimethyl sulfoxide, 100 µg/mL BSA, 8 units avian myoblastosis virus reverse transcriptase (AMV RT) (Molecular Genetics Resources), 0.1 unit *E. coli* RNase H (Pharmacia), 40 units T7 RNA polymerase (Pharmacia), 12.5 units ribonuclease inhibitor (Pharmacia), 0.04 µM Primer 1 and 0.04 µM Primer 2 in a final volume of 25 µL. In addition, each standard NASBA reaction contained a 2–1-µL aliquot of the nucleic acid sample from a hybridization reaction or just $H_2O$ as a control.

Except for a 2–1-µL aliquot of enzyme mixture comprising AMV RT, T7 RNA polymerase, *E. coli* RNase H and ribonuclease inhibitor, the remaining NASBA reaction components and nucleic acid sample or $H_2O$ for each reaction were mixed at room temperature, heated at 65° C. for 2 minutes and then transferred to a water bath at 40° C. After 2 minutes at 40° C., 2 µL of the enzyme mixture was added to each reaction tube. Incubation of the reactions was continued at 40° C. for 90 minutes.

The amplification products contained in a 5–1-µL aliquot of each amplification reaction was analysed by agarose gel electrophoresis and by Northern blot hybridization analysis (Sooknanan et al., 1993). The Northern blot membrane was hybridized following the teaching of Example 3.

Figure 3:
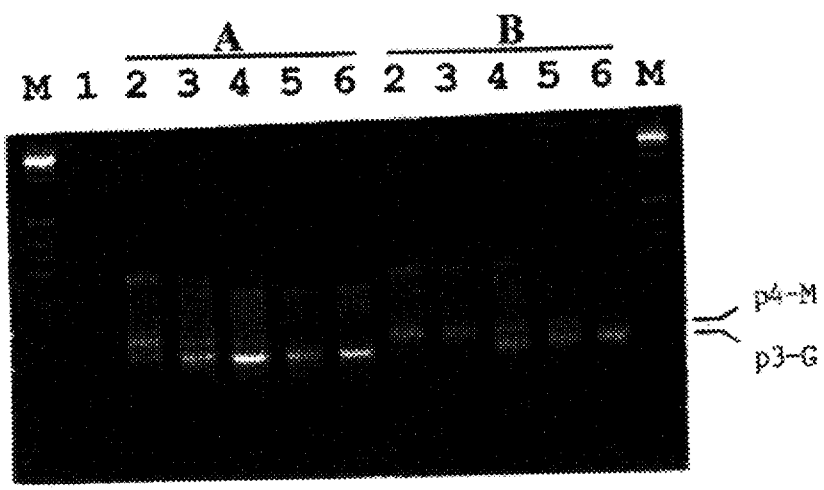
FIG. 3 shows agerose gel electrophoretic analysis of the products of subtractive amplification using NASBA, where (I) is a photograph of the products detected by ethidium bromide staining, and (II) is an autoradiogram of the products detected by blot hybridization to radiolabeled oligonucleotide probes.
Figure 3:
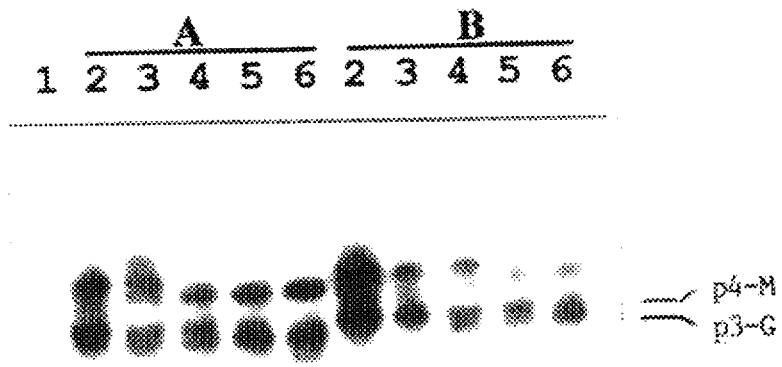

The amplified products contained in the reactions to which no pT7T3-G driver DNA was added represented simply the co-amplification of the different ratios of p3-G and p4-M RNAs (FIG. 3-I, -II; Lanes A2–6). The p4-M amplicons were not visible in those reactions where the concentration of input p3-G RNA exceeded that of p4-M by at least 1000 fold (Lanes A5–6), whereas the p3-G amplicons were visible in all of the different mixtures (Lanes A2–6).

On the other hand, when the tester RNA mixtures were exposed to the pT7T3-G driver DNA, p4-M amplicons were readily visible even when the concentration of input p3-G RNA exceeded that of p4-M by $10^5$-fold (Lane B6). In addition, p3-G amplicons were no longer visible when the concentration of input p4-M was similar to or 10-fold lower than that of p3-G (Lanes B2–3). Neither p3-G nor p4-M amplicons were seen in the reaction to which water was added instead of a nucleic acid sample (Lane 1). These results clearly indicated that the p4-M sequence was selectively enriched as a direct result of the use of pT7T3-G driver DNA to inactivate the p3-G tester RNA.

In FIG. 3-I and 3-II, the following lanes contain the following materials:

1—no added template
2—$10^8$ p3-G and $10^8$ p4-M RNA molecules
3—$10^8$ p3-G and $10^7$ p4-M RNA molecules
4—$10^8$ p3-G and $10^6$ p4-M RNA molecules
5—$10^8$ p3-G and $10^5$ p4-M RNA molecules
6—$10^8$ p3-G and $10^4$ p4-M RNA molecules
A—minus pT7T3-G driver DNA
B—plus pT7T3-G driver DNA

EXAMPLE 6

Selective enrichment of a specific nucleic acid sequence after two rounds of Subtractive Amplification using NASBA After the first round of subtractive amplification, in the reaction corresponding to lane B5 of FIG. 3 in Example 5, the p4-M sequence appeared to be enriched to approximately the same level as the p3-G sequence. As a further demonstration, a second round of subtractive amplification was performed not only to further enrich the p4-M sequence, but also to reverse the enrichment process by re-selecting for the p3-G sequence. Thus, either single-stranded pT7T3-G or pT7T3-M driver DNA was added to identical hybridization reactions containing, as tester RNA mixtures, serial 100-fold dilutions of the amplified products of the selected reaction. Standard hybridization reactions were prepared following the teaching of Example 3, each containing 2-µL the $10^{-4}$, $10^{-6}$ and $10^{-8}$ dilutions of the above mentioned first-round amplification reaction. In addition, a standard hybridization reaction containing 2 µL of the $10^{-8}$ dilution of the said first-round reaction did not receive any driver DNA as a control. The hybridization reactions were incubated following the teaching of Example 3, and then digested with 1 unit RQ DNase I endonuclease at 37° C. for 30 minutes prior to amplification.

Meanwhile, standard NASBA reactions were prepared following the teaching of Example 5, using 2-µL aliquots of the second-round hybridization reactions as tester RNA. The amplification reactions and subsequent detection of the amplified materials were performed according to the teaching of Example 5.

Figure 4:
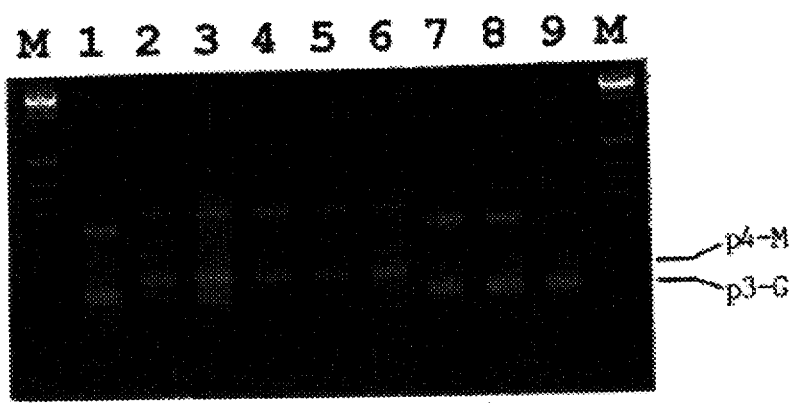
FIG. 4 shows agarose gel electrophoretic analysis of the products of the first and second rounds of subtractive amplification using NASBA, where (I) is a photograph of the products detected by ethidium bromide staining, and (II) is an autoradiogram of the products detected by blot hybridization to radiolabeled oligonucleotide probes.
Figure 4:
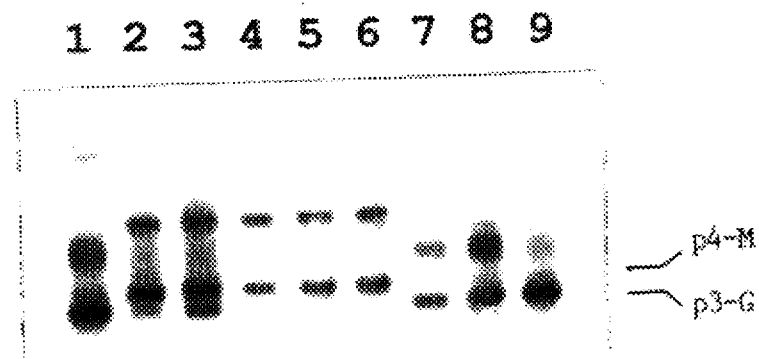

The product from the first round reaction (FIG. 4; Lane 2) when re-amplified in the absence of second-round subtraction resulted in the enrichment of both p3-G and p4-M sequences equally (Lane 3). However, after the second-round subtraction with pT7T3-G driver DNA, the p4-M sequence was predominantly amplified in all three dilutions tested (Lanes 4–6). Similarly, when pT7T3-M driver DNA was used instead for subtraction, the p3-G sequence was predominantly amplified (Lane 7–9), reaching a level comparable to that of the primary reaction without subtraction (Lane 1).

Since there was no apparent difference in the amounts of second-round p4-M amplicon generated between the $10^{-4}$, $10^{-6}$ and $10^{-8}$ dilutions of the first round reaction, 0.8 pmol of driver DNA was sufficient to inactivate the complementary tester RNA sequence over a range of concentrations differing by as much as 10,000 fold. Also, the results clearly demonstrated that the subtractive amplification process was sequence-directed because the enrichment of a particular sequence was reversible depending on the sequence of the driver DNA used for subtraction. Overall, two rounds of the subtractive amplification process were sufficient to enrich a unique sequence (p4-M) from one of a minor species to clearly the more dominant species.

In FIG. 4-I and 4-II, the following lanes contain the following materials:

1—$10^{-8}$ p3-G and $10^5$ p4-M RNA molecules minus driver DNA
2—$10^{-8}$ p3-G and $10^5$ p4-M RNA molecules plus driver DNA
3—$10^{-8}$ dilution of #2 minus driver DNA
4—$10^{-4}$ dilution of #2 plus pT7T3-G driver DNA
5—$10^{-6}$ dilution of #2 plus pT7T3-G driver DNA
6—$10^{-8}$ dilution of #2 plus pT7T3-G driver DNA
7—$10^{-4}$ dilution of #2 plus pT7T3-M driver DNA
8—$10^{-6}$ dilution of #2 plus pT7T3-M driver DNA
9—$10^{-8}$ dilution of #2 plus pT7T3-M driver DNA

EXAMPLE 7

Selective enrichment of a specific nucleic acid sequence using NASBA for the first-round and RT-PCR for the second-round of subtractive amplification The hybridization reactions described in Example 6 were used as tester RNA for the second-round subtractive amplification using RT-PCR. The RT-PCR reactions were performed following the teaching of Example 3. The products contained in a 5-µL aliquot of each amplification reaction were analysed by agarose gel electrophoresis and Southern blot hybridization analysis following the teaching of Example 3.

Figure 5:
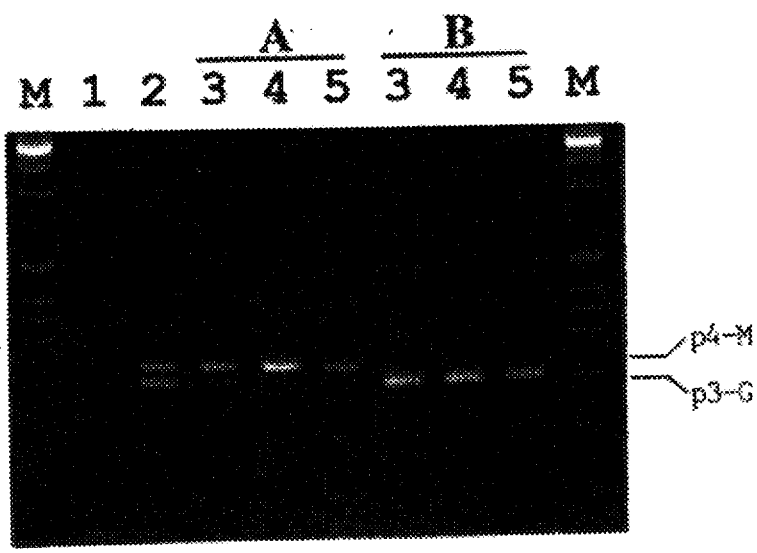
FIG. 5 shows agarose gel electrophoretic analysis of the products of a second round of subtractive amplification using PCR following a first round of subtractive amplification using NASBA, where (I) is a photograph of the products detected by ethidium bromide staining, and (II) is an autoradiogram of the products detected by hybridization to radiolabeled oligonucleotide probes.
Figure 5:
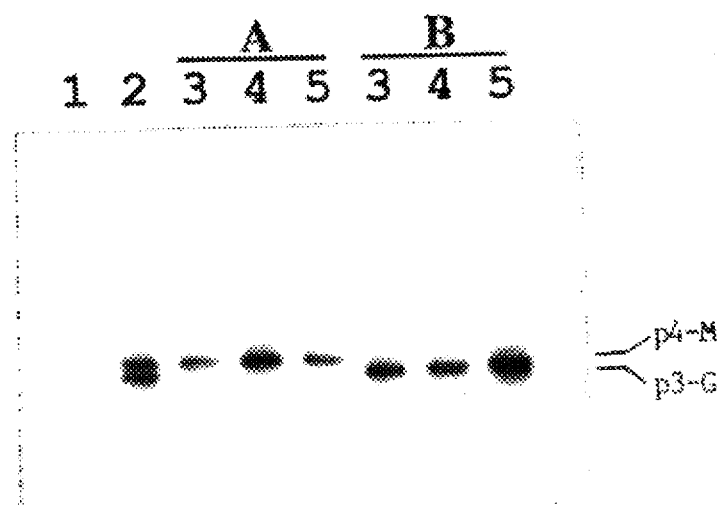

The second-round RT-PCR reaction without added driver DNA resulted in essentially equal amounts of p3-G and p4-M amplicons (FIG. 5-I, -II; Lane 2), which was similar to the first-round NASBA reaction (FIG. 3-I; Lane B5). However, after second-round subtractive amplification with pT7T3-G driver DNA, the p4-M sequence was significantly enriched in all three of the dilutions of the said first-round sample (FIG. 5-I, -II; Lanes A3–5). The three dilutions ($10^{-4}$, $10^{-6}$ and $10^{-8}$) represented an increase in the driver:tester ratio of at least 10,000-fold. Thus, if at all expected, the p3-G amplicons will be the least efficiently subtracted in the lowest dilution of the first-round sample, and indeed, a trace of p3-G amplicons was still visible in this sample after re-amplification (Lane A3).

When the reciprocal second-round subtraction was performed with pT7T3-M driver DNA, the p3-G sequence was predominantly amplified instead for all three of the dilutions tested (Lanes B3–5). Interestingly, no p4-M amplicons were visible in the case of the least diluted sample (Lane B3) compared to the same dilution with pT7T3-G driver DNA. This observation suggested that the p4-M RNA may have been more efficiently inactivated than the p3-G RNA during the hybridization reaction.

These results clearly indicate that the amplified products of a first-round subtractive amplification process using NASBA can also be readily enriched in a second-round subtractive amplification reaction using RT-PCR. In fact, it should also be possible to perform second-round NASBA starting from the product of a first-round RT-PCR reaction by following the teaching of Example 4.

In FIG. 5-I and 5-II, the following lanes contain the following materials:
1—no added template
2—$10^{-8}$ dilution of the first-round NASBA minus driver DNA
3—$10^{-4}$ dilution of the first-round NASBA plus driver DNA
4—$10^{-6}$ dilution of the first-round NASBA plus driver DNA
5—$10^{-8}$ dilution of the first-round NASBA plus driver DNA
A—pT7T3-G driver DNA
B—pT7T3-M driver DNA

EXAMPLE 8

RNase H -dependent and -independent inactivation of tester RNA sequences

A sample of a first-round subtractive amplification reaction digested with RQ DNase I, as described in Example 4, was diluted $10^8$-fold. Five standard hybridization reactions minus RNase H were prepared each containing 2 µL of the $10^{-8}$ dilution of the said reaction. In addition, pT7T3-M driver DNA was added to four of the five reactions and two of these four reactions received thermostable RNase H. All reactions were hybridized following the teaching of Example 3.

Of the two reactions containing driver DNA and no RNase H, one was digested with RQ DNase I following hybridization and prior to amplification. Also, one of the two reactions containing driver DNA and RNase H was similarly digested. Samples of the different hybridization reactions were then enriched using either RT-PCR or NASBA performed following the teachings of Examples 3 and 5, respectively.

The amplification products of the RT-PCR reactions were analysed by agarose gel electrophoresis and Southern blot hybridization (FIG. 7A-I, -II), following the teaching of Example 3, whereas the amplification products contained in 5-µL aliquots of the NASBA reactions were serially diluted and analyzed by slot-blot hybridization (Sambrook, et al., 1989) (FIG. 7B-I, -II), following the teaching of Example 5.

The amplified products of the second-round RT-PCR or NASBA reaction which did not receive any driver DNA contained essentially similar amounts of p3-G and p4-M amplicons as expected (FIGS. 7A- and B-I, -II; Lane 2). The reactions containing just pT7T3-M driver DNA in the hybridization reaction (i.e. no RNase H), however, showed a significant increase in the level of the p3-G amplicon over the p4-M amplicon (FIGS. 7A- and B-I, -II; Lane 3). Based on this result, simply annealing the p4-M RNA to its complementary driver DNA during the hybridization reaction was sufficient to block amplification of the RNA in the subsequent RT-PCR reaction.

This conclusion was further supported by results from another reaction containing driver DNA without RNase H that was digested with DNase I prior to re-amplification. In this reaction, the hybridization process appeared to have been reversed as a result of the DNase I treatment because both p:3-G and p4-M were once again re-amplified to similar levels for both RT-PCR and NASBA (FIGS. 7 A- and B-I, -II; Lane 4). Essentially, the DNase I treatment destroyed the DNA of the RNA:DNA hybrid, and in so doing, the hybridized RNA was released to be amplified.

Conversely, when driver DNA and RNase H are present in the hybridization reaction, the RNA of a RNA:DNA hybrid would become hydrolyzed. Consequently, DNase I treatment of such a reaction should not reverse the hybridization process, whereby the RNA can once again be amplified. Thus, when this was the case, the p3-G sequence was preferentially enriched over p4-M in either RT-PCR or NASBA despite the DNase I digestion (FIGS. 7A- and B-I, -II; Lanes 5–6).

Furthermore, the use of RNase H appears to also increase the efficiency of the subtraction process. That is, a minor band corresponding to the p4-M amplicon was visible after RT-PCR re-amplification of a sample not treated with RNase H compared to a similar sample containing RNase H (FIG. 7A-I, -II; Lane 3 vs Lane 5). Similarly, the slot-blot results for comparable NASBA reactions showed a greater than ten-fold increase in efficiency when RNase H was used (FIG. 7B-I; Lanes 3 vs 5). The increased efficiency with RHase H is most likely due to multiple rounds of hybrid formation and degradation of the hybridized RNA during the hybridization reaction. Thus, the use of RNase H is not absolutely essential for enablement of the subtractive amplification process.

In FIG. 7A- and B-I, -II, the following lanes contain the following materials,
1—no added template
2—$10^{-8}$ dilution of sample minus driver DNA
3—$10^{-8}$ dilution of sample plus driver DNA
4—$10^{-8}$ dilution of sample plus driver DNA plus DNase I
5—$10^{-8}$ dilution of sample plus driver DNA plus RNase H
6—$10^{-8}$ dilution of sample plus driver DNA, RNase H and DNase I

EXAMPLE 9

Subtraction levels with and without RNase H for RT-PCR and NASBA

Figure 6A:
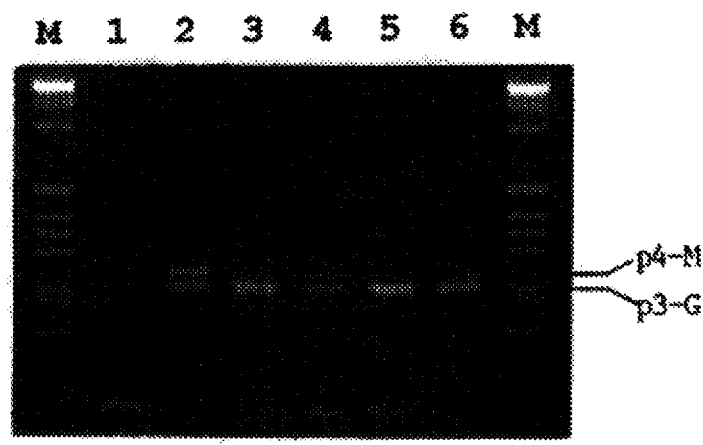
FIG. 6A shows agarose gel electrophoretic analysis of the products of subtractive amplification, wherein the hybridization reaction was variously treated with RNase H and/or DNase I before amplification using PCR, where (I) is a photograph of the products detected by ethidium bromide staining, and (II) is an autoradiogram of the products detected by blot hybridization to radiolabeled oligonucleotide probes.
Figure 6A:
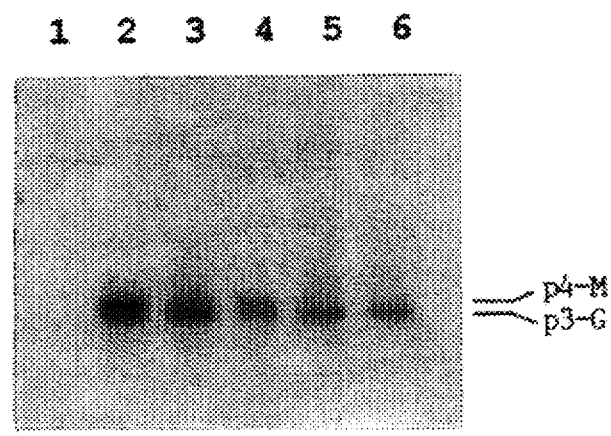
Figure 6B:
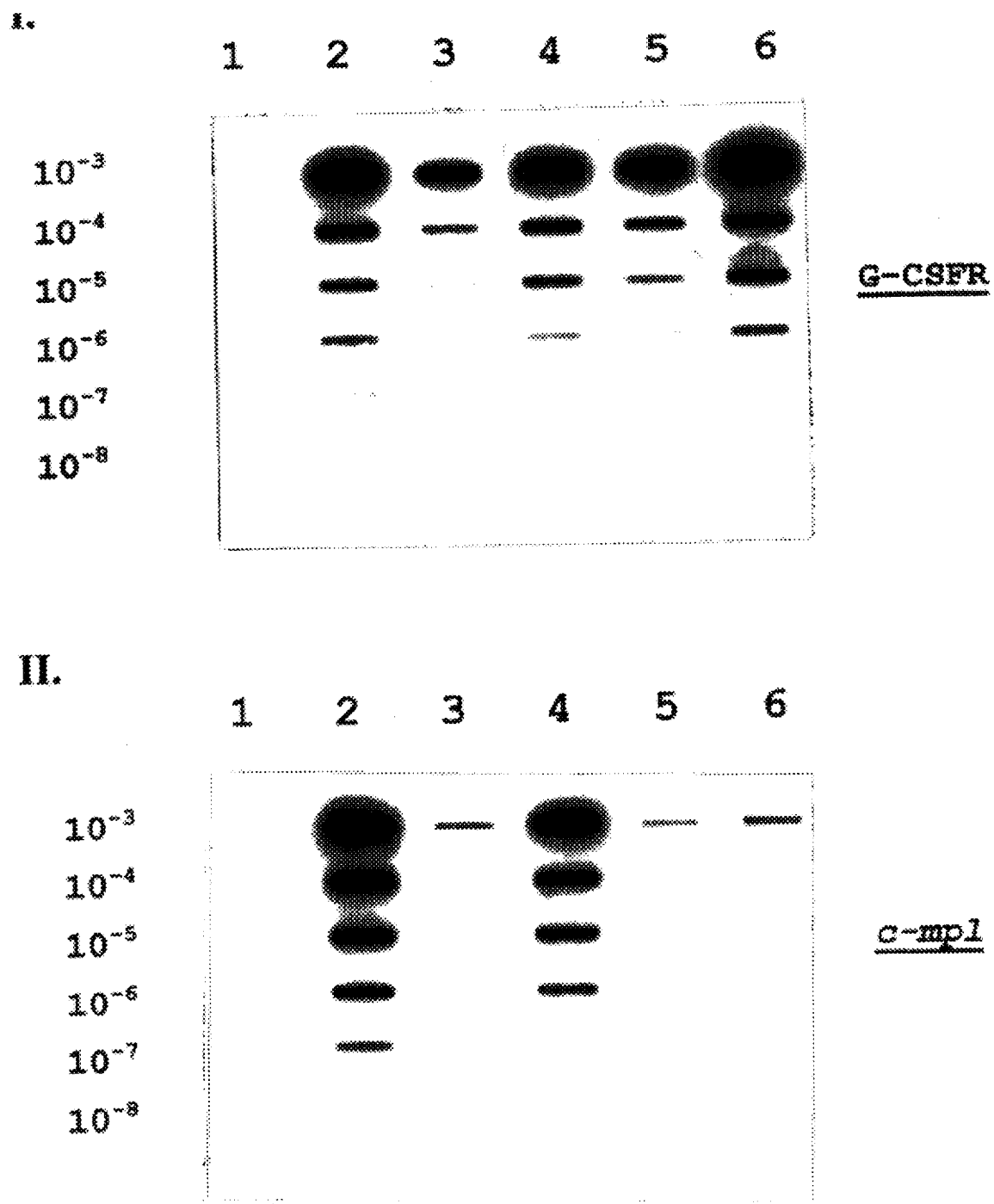
FIG. 6B shows autoradiograms of slot blot hybridization analysis of the products of subtractive amplification, wherein the hybridization reaction were variously treated with RNase H and/or DNase I before amplification using NASBA, where the products were detected by hybridization to probes specific to either (I) G-CSFR or (II) c-mpl sequences.
Figure 7:
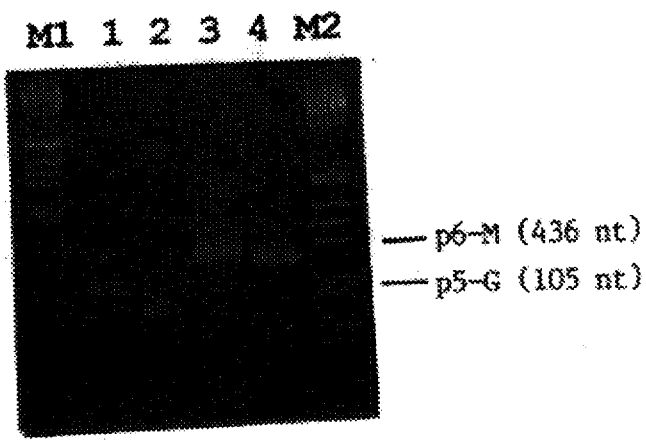
FIG. 7 shows agarose gel electrophoretic analysis of the products of transcription reactions of cDNA clones which were adapted with a P2 primer, where (I) is a photograph of the products detected by ethidium bromide staining, and (II) is an autoradiogram of the products detected by blot hybridization to radiolabeled oligonucleotide probes.
Figure 7:
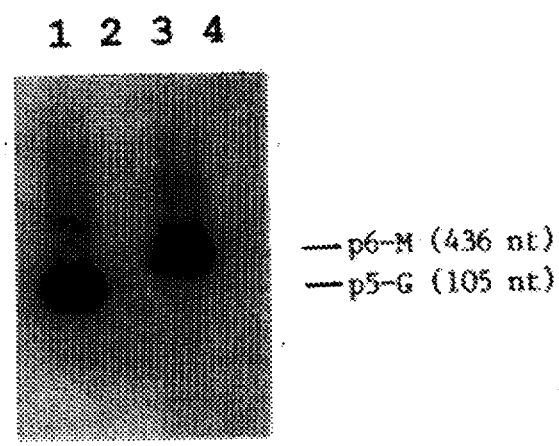

The levels of subtraction obtained with driver DNA alone or in combination with RNase H for samples #3 and #5 described in FIG. 6 in Example 8 were quantified by serial dilution and slot-blot analysis (Sambrook et al., 1989). Slotblot membranes were hybridized with either of two $^{32}$P-labelled probes (SEQ. ID. NO. 3 and 4). The hybridized membranes were then dissected into individual slots and the radioisotope contained in each slot was measured in a scintillation counter. Based on the ratios of p3-G to p4-M amplicons obtained after hybridization for each sample, the levels of enrichment, and thus the relative subtraction efficiencies, were determined.

The presence of RNase H in the standard subtractive amplification reaction resulted in a 3- to 4-fold enrichment of the tester sequence in either NASBA or RT-PCR (Table 3). The improvement in subtraction with RNase H is attributed to multiple rounds of degradation of the RNA of a RNA:DNA tester-driver complex by RNase H because the same driver DNA can repeatedly bind a new RNA molecule once the previous RNA molecule has been degraded. The ensuing cycles of hybrid formation and degradation of the RNA will increase the efficiency of subtraction compared to the single hybridization-inactivation event with only driver DNA. These results confirm those of Example 8, in that the subtractive amplification process operates independently of RNase H.

EXAMPLE 10

P2-adaptation of cDNA clones

Plasmid DNA, isolated from cDNA-recombinants p5-G and p6-G, were digested to completion with restriction endonuclease Sau3AI (New England Biolabs), and 0.1 pmol of each was added to separate ligation reactions containing 50 mM Tris-HCl (pH 7.5), 10 mM MgCl$_2$, 1 mM ATP, 5 mM DTT, 1 mg/mL BSA, 1 pmol Primer 2, 1 pmol P2-adaptor (SEQ. ID. NO. 21) and 2.5 units T4 DNA ligase (Bethesda Research Labs.) in a final volume of 20 µL. In addition, DNA ligase was omitted from a second set of similar reactions. The reaction components were assembled at room temperature, heated at 65° C. for 2 minutes and incubated at room temperature (~22° C.) for 60 minutes.

Next, standard transcription reactions were prepared, according to the teaching of Example 2, containing a final concentration of 15 mM MgCl$_2$ and 25% of a ligation reaction described above. After incubating the reactions at 37° C. for 60 minutes, 1 unit RQ DNase I was added to each and incubation was continued at 37° C. for 30 minutes. The RNA transcripts synthesized in each reaction were desalted and the concentration of each was measured at A$_{260}$ nm. In addition, 10% of each transcription reaction was analysed by native agarose gel electrophoresis and northern blot hybridization using $^{32}$P-labelled Primer 2 (SEQ. ID. NO. 12) as the probe.

The RNA transcripts from the reactions to which DNA ligase was added corresponded to the expected sizes for p5-G (105 nt) and p6-M (436 nt) (SEQ. ID. Nos. 24 and 25, Table 5), based on the location of the first Sau3AI site from the 5' end of the respective cDNA fragment and the length of the Primer 2 sequence (FIG. 7-I; Lanes 1 and 3). On the other hand, the reactions to which no DNA ligase was added produced RNA transcripts that were shorter in length, likely due to the absence of the Primer 2 sequence (Lanes 2 and 4). As expected, only the P2-adapted RNA transcripts hybridized to Primer 2 when used as the probe (Lanes 1 vs 2 and 3 vs 4). In addition, the P2-adapted RNA transcripts were amplifiable both by NASBA and RT-PCR with primers 1 and 2.

In FIG. 9-I and 9-II, the following lanes contain the following materials,
1—Sau3AI digested p5 DNA plus T4 DNA ligase
2—Sau3AI digested p5 DNA minus T4 DNA ligase
3—Sau3AI digested p6 DNA plus T4 DNA ligase
4—Sau3AI digested p6 DNA minus T4 DNA ligase
M—M.W. marker for Lanes 1 and 2
M—M.W. marker for Lanes 3 and 4

EXAMPLE 11

Application of the Subtractive Amplification process to the P2-adapted RNA transcripts The P2-adapted transcripts for p5-G and p6-M recombinants prepared according to the teaching of Example 10 were serially diluted in H$_2$O. Standard hybridization reactions were prepared following the teaching of Example 3 with the exception that the tester RNA comprised various mixtures of the P2-adapted p5-G and p6-M in which, the concentration of p5-G RNA was kept constant at 1.7 amol ($10^6$ molecules) and the concentration of the p6-M RNA was increased from 0.016 amol ($10^4$ molecules) to 1.6 amol ($10^6$ molecules) in 10-fold increments (set B). As a control, the pT7T3-G driver DNA was not added to a second set of identical hybridization reactions (set A). The hybridization reactions were all incubated following the teaching of Example 3.

Meanwhile, standard RT-PCR reactions were prepared following the teaching of Example 3 with the exception that all components of each reaction was reduced by 50%. The amplification reactions and subsequent detection of the amplified materials were performed also following the teaching of Example 3 with the exception that the Southern blot was hybridized with [5'-$^{32}$P] oligonucleotide probes (SEQ. ID. NO. 22 and SEQ. ID. NO. 23) specific to either the p5-G amplicons (SEQ. ID. NO. 24) or the p6-M amplicons (SEQ. ID. NO. 25).

Figure 8:
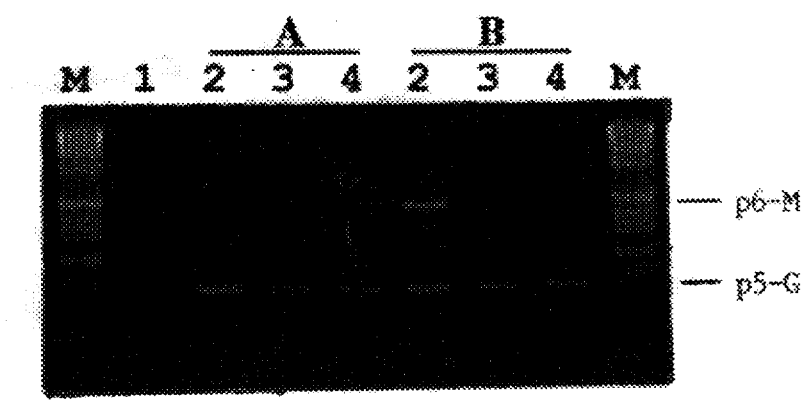
FIG. 8 shows agarose gel electrophoretic analysis of the products of subtractive amplification using PCR, where (I) is a photograph of the products detected by ethidium bromide staining, and (II) is an autoradiogram of the products detected by blot hybridization to radiolabeled oligonucleotide probes.
Figure 8:
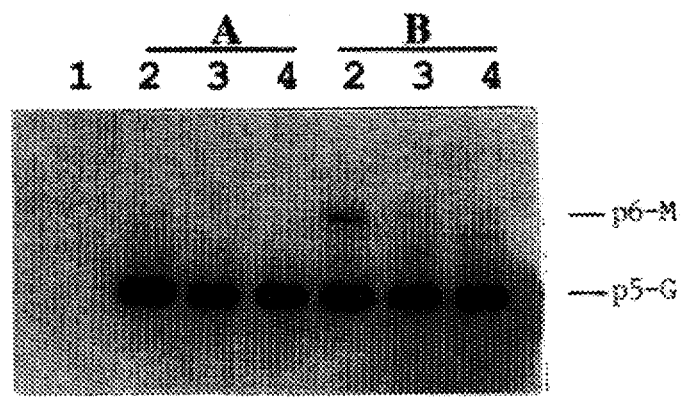

The relative co-amplification of the P2-adapted p5-G and p6-G transcripts independent of subtraction is shown in FIG. 8-I, II; Lanes A2-4. Of the three mixtures of p5-G and p6-M transcripts, only the one containing an equal amount of each transcript produced both amplicons after RT-PCR amplification (Lane A2). For the other two mixtures, only the p5-G amplicon was seen (Lanes A3-4).

However, when similar RNA mixtures were subjected to subtraction with the pT7T3-G driver DNA, the copy number of the p6-M amplicon increased relative to that for p5-G in the mixture containing an equal amount of the two RNA transcripts (Lane B2). In addition, the p6-M amplicon was also now visible by both ethidium bromide staining and Southern hybridization in the reaction containing a 10-fold excess of p5-G RNA over p6-M RNA (Lane B3) and by Southern hybridization in the reaction containing a 100-fold excess of the p5-G RNA (Lane B4). The p5-G amplicon was still amplified in all the different RNA mixtures (Lanes B2-4). Neither p5-G nor p6-M sequences were seen in the reaction where water was added instead of a nucleic acid sample (Lane 1). These results clearly showed significant enrichment of the P2-adapted p6-M sequence following inactivation of the p5-G sequence with pT7T3-G driver DNA.

In FIG. 8-I and 8-II, the following lanes contain the following materials,
1—no added template
2—$10^6$ p5-G and $10^6$ p6-M RNA molecules
3—$10^6$ p5-G and $10^5$ p6-M RNA molecules
4—$10^6$ p5-G and $10^4$ p6-M RNA molecules
A—minus driver DNA
B—plus T7T3-G driver DNA Although preferred embodiments of the invention have been described in detail, it will be understood by those skilled in the art that variations may be made thereto without departing from either the spirit of the invention or the scope of the appended claims.

TABLE 1

| Sequence I.D. No. | Sequence (5' → 3') | Description |
|---|---|---|
| 3 | AAA AAT GCA TTG GAG TGC GGG CAC ATC AGT GT | gcsfrfwd.pcr |
| 4 | TTT CAA GCT TAG GCA TGC GTT CTC AGC TCC AGG CT | gcsfrrev.pcr |
| 5 | AAA ATG CAT CGC AAG ATG TCT CCT TGC TGG CA | mplfwd1a.pcr |
| 6 | AGA AGA AGC CTT GGG AGC TA | mplrev1a.pcr |
| 7 | CAA TGG CAG CAA CAG GAC CA | mplfwd2a.pcr |
| 8 | AAA AAG CTT CAG CTC GAG GAG GCG GTC TCG GTG GCG GTC T | mplrev2a.pcr |

TABLE 2

| Sequence I.D. No. | Sequence (5' → 3') | Description |
|---|---|---|
| 9 | TCG AGC TAG CGG CCG CAT AGT AAT GCA TAG ATC TCC AGT GAT TTT TTT CTC CAT CTC CCT ATA GTG AGT CGT ATT AG | catcon1 |
| 10 | GAT CTA TGC ATT ACT ATG CGG CCG CTA GCT CGA GTG ATA ATA AGC GGA TGA ATG GCT GCA | catcon2 |
| 11 | AAT TCT AAT ACG ACT CAC TAT AGG GAG ATG GAG AAA AAA ATC ACT GGA | Primer 1 (P1) |
| 12 | GCC ATT CAT CCG CTT ATT ATC AC | Primer 2 (P2) |
| 13 | CGC GTG GCG CGC CAT TAA TTA ATG CGG CCG | OGS-3 |
| 14 | CTA GCG GCC GCA TTA ATT AAT GGC GCG CCA CGC GTC CAG TGA TTT TTT TCT CCA TCT CCC TAT AGT GAG TCG TAT TAG | OGS-9 |
| 19 | CTG GGT CCC ATC AGA CAG ACG CTG CTG C | G-CSFR |
| 20 | CTG CAT CTC CAG GCA GGT CCA CAG TCA C | c-mpl |
| 21 | GAT CGT GAT AAT AAG CG | OGS-12 |
| 22 | TGA TGT GCC CGC ACT CCA ATG CAC GCG | OGS-15 |
| 23 | AGC AAG GAG ACA TCT TGC GAT GCA GCG | OGS-16 |

TABLE 3

| Sequence I.D. No. | Sequence (5' → 3') | Description |
|---|---|---|
| 15 | GGGAGATGGA GAAAAAAATC ACTGGAGATC TATGCAGCCA TCTGGACCCG GAGCCACAGA TTCTGTGGAG ACTGGGAGCA GAGCTTCAGC CCGGGGGCAG GCAGCAGCGT CTGTCTGATG GGACCCAGGA ATCTATCATC ACCCTGCCCC ACCTCAACCA CACTCAGGGG CTAGCTCGAG TGATAATAAG CGGATGAATG GC | P3-G RNA |
| 16 | GCCATTCATC CGCTTATTAT CACTCGAGCT AGCCCCTGAG TGTGGTTGAG GTGGGGCAGG GTGATGATAG ATTCCTGGGT CCCATCAGAC AGACGCTGCT GCCTGCCCCC GGGCTGAAGC TCTGCTCCCA GTCTCCACAG AATCTGTGGC TCCGGGTCCA GATGGCTGCA TAGATCTCCA GTGATTTTTT TCTCCATCTC CC | P3-G cDNA |
| 17 | GGGAGATGGA GAAAAAAATC ACTGGAGATC TATGCAGCTG | P4-M |

TABLE 3-continued

| Sequence I.D. No. | Sequence (5' → 3') | Description |
|---|---|---|
|  | CGCAGCGAAC CTGATGGGAT CTCCCTCGGT GGCTCCTGGG GATCCTGGTC CCTCCCTGTG ACTGTGGACC TGCCTGGAGA TGCAGTGGCA CTTGGACTGC AATGCTTTAC CTTGGACCTG AAGAATGTTA CCTGTCAATG GCAGCAACAG GACCATGCTA GCTCGAGTGA TAATAAGCGG ATGAATGGC | RNA |
| 18 | GCCATTCATC CGCTTATTAT CACTCGAGCT AGCATGGTCC TGTTGCTGCC ATTGACAGGT AACATTCTTC AGGTCCAAGG TAAAGCATTG CAGTCCAAGT GCCACTGCAT CTCCAGGCAG GTCCACAGTC ACAGGGAGGG ACCAGGATCC CCAGGAGCCA CCGAGGGAGA TCCCATCAGG TTCGCTGCGC AGCTGCATAG ATCTCCAGTG ATTTTTTTCT CCATCTCCC | P4-M cDNA |

TABLE 4

Effect of RNase H

| Method | Fold Enrichment of Target | | Ratio |
|---|---|---|---|
|  | (−RNase H) | (+RNase H) | (+RNase H):(−RNase H) |
| RT-PCR | 5.53 | 16.16 | 2.92 |
| NASBA | 7.20 | 32.05 | 4.45 |

TABLE 5

| Sequence I.D. No. | Sequence (5' → 3') | Description |
|---|---|---|
| 24 | GGGAGATGGA GAAAAAAATC ACTGGACGCG TGCATTGGAG TGCGGGCACA TCAGTGTCTC AGCCCCCATC GTCCACCTGG GGGATCGTGA TAATAAGCGG ATGAATGGC | P5-G RNA |
| 25 | GGGAGATGGA GAAAAAAATC ACTGGACGCG TGCATCGCAA GATGTCTCCT TGCTGGCATC AGACTCAGAG CCCCTGAAGT GTTTCTCCCG AACATTTGAG GACCTCACTT GCTTCTGGGA TGAGGAAGAG GCAGCGCCCA GTGGGACATA CCAGCTGCTG TATGCCTACC CGCGGGAGAA GCCCCGTGCT TGCCCCCTGA GTTCCCAGAG CATGCCCCAC TTTGGAACCC GATACGTGTG CCAGTTTCCA GACCAGGAGG AAGTGCGTCT CTTCTTTCCG CTGCACCTCT GGGTGAAGAA TGTGTTCCTA AACCAGACTC GGACTCAGCG AGTCCTCTTT GTGGACAGTG TAGGCCTGCC GGCTCCCCCC AGTATCATCA AGGCCATGGG TGGGAGCCAG CCAGGGGAAC TTCAGATCGT GATAATAAGC GGATGAATGG C | P6-M RNA |
| 26 | GCCATTCATC CGCTTATTAT CACGATCCCC CAGGTGGACG ATGGGGGCTG AGACACTGAT GTGCCCGCAC TCCAATGCAC GCGTCCAGTG ATTTTTTTCT CCATCTCCC | P5-G cDNA |
| 27 | GATCGCCATT CATCCGCTTA TTATCACGAT CTGAAGTTCC CCTGGCTGGC TCCCACCCAT GGCCTTGATG ATACTGGGGG GAGCCGGCAG GCCTACACTG TCCACAAAGA GGACTCGCTG AGTCCGAGTC TGGTTTAGGA ACACATTCTT CACCCAGAGG TGCAGCGGAA AGAAGAGACG CACTTCCTCC TGGTCTGGAA ACTGGCACAC GTATCGGGTT CCAAAGTGGG GCATGCTCTG GGAACTCAGG GGGCAAGCAC GGGGCTTCTC CCGCGGGTAG GCATACAGCA GCTGGTATGT CCCACTGGGC GCTGCCTCTT CCTCATCCCA GAAGCAAGTG AGGTCCTCAA ATGTTCGGGA GAAACACTTC AGGGGCTCTG AGTCTGATGC CAGCAAGGAG ACATCTTGCG ATGCACGCGT CCAGTGATTT TTTTCTCCAT CTCCC | P6-M cDNA |

What is claimed is:

1. A subtractive amplification method for preferentially amplifying target RNA relative to non-target RNA in a sample of tester RNA, the method comprising;

a) contacting a sample of tester RNA with driver nucleic acids under hybridizing conditions, wherein tester RNA which hybridizes to driver nucleic acids is non-target RNA and is inhibited by the hybridized driver nucleic acids from functioning as a template for reverse transcription, and wherein tester RNA which does not hybridize to driver nucleic acids comprises target RNA;

b) reverse transcribing the target RNA using a first primer to form a DNA template complementary to at least a portion of the target RNA;

c) forming an extended DNA template comprising an RNA polymerase promoter sequence by extending the 3' end of the DNA template using a hybridized promoter template; and d) transcribing the extended DNA template formed in step c) to form synthetic target RNA.

2. The method according to claim 1, wherein step a) further comprises inactivating the non-target RNA by rendering the non-target RNA incapable of functioning as a template for reverse transcription.

3. The method according to claim 1, wherein the DNA template is rendered single stranded prior to step c) by digesting target RNA hybridized to the DNA template.

4. The method according to claim 1, wherein the DNA template is rendered single stranded prior to step c) by performing strand separation.

5. The method according to claim 1, further comprising the steps of:

e) contacting the synthetic target RNA formed in step d) with a second set of driver nucleic acids under hybridizing conditions;

f) reverse transcribing synthetic target RNA which does not hybridize to the second set of driver nucleic acids in step e) to form DNA complementary to at least a portion of the synthetic target RNA; and g) copying the DNA formed in step f) to form double stranded DNA.

6. The method according to claim 1 wherein the driver sequences nucleic acids are DNA.

7. The method according to claim 2, wherein step a) further comprises digesting non-target RNA hybridized to a driver nucleic acid.

8. The method according to claim 7, wherein digesting non-target RNA hybridized to a driver nucleic acid is performed using a ribonuclease.

9. The method according to claim 8, wherein the ribonuclease is ribonuclease H.

10. The method according to claim 1, wherein the first primer is DNA.

11. The method according to claim 1, wherein reverse transcription is performed using reverse transcriptase.

12. The method according to claim 3 wherein digesting target RNA hybridized to the DNA template is performed using a ribonuclease.

13. The method according to claim 4, wherein strand separation is performed by heat denaturation.

14. The method according to claim 1, wherein the promoter template is DNA.

15. The method according to claim 14, wherein the promoter template includes sequences encoding a promoter and a transcription initiation site from a bacteriophage.

16. The method according to claim 15, wherein the bacteriophage is T7.

17. The method according to claim 1, wherein extending the DNA template in step c) is performed using a DNA polymerase.

18. The method according to claim 1, further including the step of amplifying the DNA template formed in step b).

19. The method according to claim 18, wherein amplification is performed by a polymerase chain reaction.

20. The method according to claim 1, further including the step of amplifying the extended DNA formed in step c) template.

21. The method according to claim 20, wherein amplification is performed by a polymerase chain reaction.

22. The method according to claim 1 wherein the synthetic target RNA is synthesized by a RNA amplification reaction.

23. The method according to claim 22, wherein amplification is performed by NASBA.

24. The method according to claim 1, wherein transcription is performed using a bacteriophage RNA polymerase.

25. The method according to claim 1, wherein the sample of tester RNA is synthetic target RNA obtained by a method of substractive amplification.

26. A subtractive amplification method for preferentially amplifying target RNA relative to non-target RNA in a sample of tester RNA, the method comprising:
   a) contacting a sample of tester RNA with driver nucleic acids under hybridizing conditions, wherein tester RNA which hybridizes to driver nucleic acids is non-target RNA and is inhibited by the hybridized driver nucleic acids from functioning as a template for reverse transcription, and wherein tester RNA which does not hybridize to driver nucleic acids comprises target RNA;
   b) contacting the target RNA with nucleic acid primers under hybridizing conditions;
   c) reverse transcribing the target RNA using the hybridized primers to form a DNA template complementary to at least a portion of the target RNA;
   d) rendering the DNA template single stranded;
   e) contacting the single stranded DNA template with a promoter template under hybridizing conditions;
   f) forming an extended DNA template comprising an RNA polymerase promoter sequence by extending the 3' end of the DNA template using the hybridized promoter template; and
   g) transcribing the extended DNA template of step f) to form synthetic target RNA.

27. A subtractive amplification method for preferentially amplifying target RNA relative to non-target RNA in a sample of tester RNA, both the target and non-target RNA containing terminal priming sequences for amplification, the method comprising:
   a) contacting a sample of tester RNA with driver nucleic acids under hybridizing conditions, wherein tester RNA which hybridizes to driver nucleic acids is non-target RNA and is inhibited by the hybridized driver nucleic acids from functioning as a template for reverse transcription, and wherein tester RNA which does not hybridize to driver nucleic acids comprises target RNA;
   b) reverse transcribing the target RNA using nucleic acid primers that hybridize to the target RNA to form a DNA template complementary to at least a portion of the target RNA;
   c) forming an extended DNA template comprising a functional double stranded RNA polymerase promoter by rendering the DNA template formed in step b) single stranded and extending the 3' end of the DNA template using a hybridized promoter template; and
   d) transcribing the extended DNA template formed in step c) with an RNA polymerase to form one or more copies of synthetic target RNA.

* * * * *

SEQUENCE LISTING ( 1 ) GENERAL INFORMATION:

( i i i ) NUMBER OF SEQUENCES: 27

( 2 ) INFORMATION FOR SEQ ID NO: 1:

( i ) SEQUENCE CHARACTERISTICS:
( A ) LENGTH: 17 nucleotides
( B ) TYPE: nucleic acid
( C ) STRANDEDNESS: single
( D ) TOPOLOGY: linear ( x i ) SEQUENCE DESCRIPTION: SEQ ID NO: 1:

TAATACGACT CACTATA                                                                              17

( 2 ) INFORMATION FOR SEQ ID NO: 2:

( i ) SEQUENCE CHARACTERISTICS:
( A ) LENGTH: 28 nucleotides
( B ) TYPE: nucleic acid
( C ) STRANDEDNESS: single
( D ) TOPOLOGY: linear ( x i ) SEQUENCE DESCRIPTION: SEQ ID NO: 2:

AATTCTAATA CGACTCACTA TAGGGAGA                                                                  28

( 2 ) INFORMATION FOR SEQ ID NO: 3:

( i ) SEQUENCE CHARACTERISTICS:
( A ) LENGTH: 32 nucleotides
( B ) TYPE: nucleic acid
( C ) STRANDEDNESS: single
( D ) TOPOLOGY: linear ( x i ) SEQUENCE DESCRIPTION: SEQ ID NO: 3:

AAAAATGCAT TGGAGTGCGG GCACATCAGT GT                                                             32

( 2 ) INFORMATION FOR SEQ ID NO:4:

( i ) SEQUENCE CHARACTERISTICS:
( A ) LENGTH: 35 nucleotides
( B ) TYPE: nucleic acid
( C ) STRANDEDNESS: single
( D ) TOPOLOGY: linear ( x i ) SEQUENCE DESCRIPTION: SEQ ID NO: 4:

TTTCAAGCTT AGGCATGCGT TCTCAGCTCC AGGCT                                                          35

( 2 ) INFORMATION FOR SEQ ID NO:5:

( i ) SEQUENCE CHARACTERISTICS:
( A ) LENGTH: 32 nucleotides
( B ) TYPE: nucleic acid
( C ) STRANDEDNESS: single
( D ) TOPOLOGY: linear ( x i ) SEQUENCE DESCRIPTION: SEQ ID NO: 5:

AAAATGCATC GCAAGATGTC TCCTTGCTGG CA                                                             32

( 2 ) INFORMATION FOR SEQ ID NO:6:

( i ) SEQUENCE CHARACTERISTICS:
( A ) LENGTH: 20 nucleotides
( B ) TYPE: nucleic acid
( C ) STRANDEDNESS: single
( D ) TOPOLOGY: linear ( x i ) SEQUENCE DESCRIPTION: SEQ ID NO: 6:

AGAAGAAGCC TTGGGAGCTA 20

( 2 ) INFORMATION FOR SEQ ID NO:7:

( i ) SEQUENCE CHARACTERISTICS:
        ( A ) LENGTH: 20 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 7:

CAATGGCAGC AACAGGACCA 20

( 2 ) INFORMATION FOR SEQ ID NO:8:

( i ) SEQUENCE CHARACTERISTICS:
        ( A ) LENGTH: 40 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 8:

AAAAAGCTTC AGCTCGAGGA GGCGGTCTCG GTGGCGGTCT 40

( 2 ) INFORMATION FOR SEQ ID NO:9:

( i ) SEQUENCE CHARACTERISTICS:
        ( A ) LENGTH: 77 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 9:

TCGAGCTAGC GGCCGCATAG TAATGCATAG ATCTCCAGTG ATTTTTTCT 50

CCATCTCCCT ATAGTGAGTC GTATTAG 77

( 2 ) INFORMATION FOR SEQ ID NO:10:

( i ) SEQUENCE CHARACTERISTICS:
        ( A ) LENGTH: 60 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 10:

GATCTATGCA TTACTATGCG GCCGCTAGCT CGAGTGATAA TAAGCGGATG 50

AATGGCTGCA 60

( 2 ) INFORMATION FOR SEQ ID NO:11:

( i ) SEQUENCE CHARACTERISTICS:
        ( A ) LENGTH: 48 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 11:

AATTCTAATA CGACTCACTA TAGGGAGATG GAGAAAAAA TCACTGGA 48

( 2 ) INFORMATION FOR SEQ ID NO:12:

( i ) SEQUENCE CHARACTERISTICS:
        ( A ) LENGTH: 23 nucleotides
        ( B ) TYPE: nucleic acid ( C ) STRANDEDNESS: single
( D ) TOPOLOGY: linear ( x i ) SEQUENCE DESCRIPTION: SEQ ID NO: 12:

GCCATTCATC CGCTTATTAT CAC    23

( 2 ) INFORMATION FOR SEQ ID NO:13:

( i ) SEQUENCE CHARACTERISTICS:
( A ) LENGTH: 30 nucleotides
( B ) TYPE: nucleic acid
( C ) STRANDEDNESS: single
( D ) TOPOLOGY: linear ( x i ) SEQUENCE DESCRIPTION: SEQ ID NO: 13:

CGCGTGGCGC GCCATTAATT AATGCGGCCG    30

( 2 ) INFORMATION FOR SEQ ID NO:14:

( i ) SEQUENCE CHARACTERISTICS:
( A ) LENGTH: 78 nucleotides
( B ) TYPE: nucleic acid
( C ) STRANDEDNESS: single
( D ) TOPOLOGY: linear ( x i ) SEQUENCE DESCRIPTION: SEQ ID NO: 14:

CTAGCGGCCG CATTAATTAA TGGCGCGCCA CGCGTCCAGT GATTTTTTC    50

TCCATCTCCC TATAGTGAGT CGTATTAG    78

( 2 ) INFORMATION FOR SEQ ID NO:15:

( i ) SEQUENCE CHARACTERISTICS:
( A ) LENGTH: 202 nucleotides
( B ) TYPE: nucleic acid
( C ) STRANDEDNESS: single
( D ) TOPOLOGY: linear ( x i ) SEQUENCE DESCRIPTION: SEQ ID NO: 15:

GGGAGATGGA GAAAAAATC ACTGGAGATC TATGCAGCCA TCTGGACCCG    50

GAGCCACAGA TTCTGTGGAG ACTGGAGCA GAGCTTCAGC CGGGGGCAG    100

GCAGCAGCGT CTGTCTGATG GGACCCAGGA ATCTATCATC ACCCTGCCCC    150

ACCTCAACCA CACTCAGGGG CTAGCTCGAG TGATAATAAG CGGATGAATG    200

GC    202

( 2 ) INFORMATION FOR SEQ ID NO:16:

( i ) SEQUENCE CHARACTERISTICS:
( A ) LENGTH: 202 nucleotides
( B ) TYPE: nucleic acid
( C ) STRANDEDNESS: single
( D ) TOPOLOGY: linear ( x i ) SEQUENCE DESCRIPTION: SEQ ID NO: 16:

GCCATTCATC CGCTTATTAT CACTCGAGCT AGCCCCTGAG TGTGGTTGAG    50

GTGGGGCAGG GTGATGATAG ATTCCTGGGT CCCATCAGAC AGACGCTGCT    100

GCCTGCCCCC GGGCTGAAGC TCTGCTCCCA GTCTCCACAG AATCTGTGGC    150

TCCGGGTCCA GATGGCTGCA TAGATCTCCA GTGATTTTTT TCTCCATCTC    200

CC    202

( 2 ) INFORMATION FOR SEQ ID NO:17:

```
     ( i ) SEQUENCE CHARACTERISTICS:
             ( A ) LENGTH: 229 nucleotides
             ( B ) TYPE: nucleic acid
             ( C ) STRANDEDNESS: single
             ( D ) TOPOLOGY: linear ( x i ) SEQUENCE DESCRIPTION: SEQ ID NO: 17:

GGGAGATGGA   GAAAAAAATC   ACTGGAGATC   TATGCAGCTG   CGCAGCGAAC          50

CTGATGGGAT   CTCCCTCGGT   GGCTCCTGGG   GATCCTGGTC   CCTCCCTGTG         100

ACTGTGGACC   TGCCTGGAGA   TGCAGTGGCA   CTTGGACTGC   AATGCTTTAC         150

CTTGGACCTG   AAGAATGTTA   CCTGTCAATG   GCAGCAACAG   GACCATGCTA         200

GCTCGAGTGA   TAATAAGCGG   ATGAATGGC                                   229

( 2 ) INFORMATION FOR SEQ ID NO:18:

( i ) SEQUENCE CHARACTERISTICS:
             ( A ) LENGTH: 229 nucleotides
             ( B ) TYPE: nucleic acid
             ( C ) STRANDEDNESS: single
             ( D ) TOPOLOGY: linear ( x i ) SEQUENCE DESCRIPTION: SEQ ID NO: 18:

GCCATTCATC   CGCTTATTAT   CACTCGAGCT   AGCATGGTCC   TGTTGCTGCC          50

ATTGACAGGT   AACATTCTTC   AGGTCCAAGG   TAAAGCATTG   CAGTCCAAGT         100

GCCACTGCAT   CTCCAGGCAG   GTCCACAGTC   ACAGGGAGGG   ACCAGGATCC         150

CCAGGAGCCA   CCGAGGGAGA   TCCCATCAGG   TTCGCTGCGC   AGCTGCATAG         200

ATCTCCAGTG   ATTTTTTTCT   CCATCTCCC                                   229

( 2 ) INFORMATION FOR SEQ ID NO:19:

( i ) SEQUENCE CHARACTERISTICS:
             ( A ) LENGTH: 28 nucleotides
             ( B ) TYPE: nucleic acid
             ( C ) STRANDEDNESS: single
             ( D ) TOPOLOGY: linear ( x i ) SEQUENCE DESCRIPTION: SEQ ID NO: 19:

CTGGGTCCCA   TCAGACAGAC   GCTGCTGC                                      28

( 2 ) INFORMATION FOR SEQ ID NO:20:

( i ) SEQUENCE CHARACTERISTICS:
             ( A ) LENGTH: 28 nucleotides
             ( B ) TYPE: nucleic acid
             ( C ) STRANDEDNESS: single
             ( D ) TOPOLOGY: linear ( x i ) SEQUENCE DESCRIPTION: SEQ ID NO: 20:

CTGCATCTCC   AGGCAGGTCC   ACAGTCAC                                      28

( 2 ) INFORMATION FOR SEQ ID NO:21:

( i ) SEQUENCE CHARACTERISTICS:
             ( A ) LENGTH: 17 nucleotides
             ( B ) TYPE: nucleic acid
             ( C ) STRANDEDNESS: single
             ( D ) TOPOLOGY: linear ( x i ) SEQUENCE DESCRIPTION: SEQ ID NO: 21:

GATCGTGATA   ATAAGCG                                                    17

( 2 ) INFORMATION FOR SEQ ID NO:22:
```

( i ) SEQUENCE CHARACTERISTICS:
    ( A ) LENGTH: 27 nucleotides
    ( B ) TYPE: nucleic acid
    ( C ) STRANDEDNESS: single
    ( D ) TOPOLOGY: linear ( x i ) SEQUENCE DESCRIPTION: SEQ ID NO: 22:

AGCAAGGAGA CATCTTGCGA TGCAGCG                                    27

( 2 ) INFORMATION FOR SEQ ID NO:23:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 23:

AGCAAGGAGA CATCTTGCGA TGCAGCG                                    27

( 2 ) INFORMATION FOR SEQ ID NO:24:

( i ) SEQUENCE CHARACTERISTICS:
        ( A ) LENGTH: 109 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 24:

GGGAGATGGA GAAAAAAATC ACTGGACGCG TGCATTGGAG TGCGGGCACA            50

TCAGTGTCTC AGCCCCCATC GTCCACCTGG GGGATCGTGA TAATAAGCGG            100

ATGAATGGC                                                        109

( 2 ) INFORMATION FOR SEQ ID NO:25:

( i ) SEQUENCE CHARACTERISTICS:
        ( A ) LENGTH: 441 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 25:

GGGAGATGGA GAAAAAAATC ACTGGACGCG TGCATCGCAA GATGTCTCCT            50

TGCTGGCATC AGACTCAGAG CCCCTGAAGT GTTTCTCCCG AACATTTGAG            100

GACCTCACTT GCTTCTGGGA TGAGGAAGAG GCAGCGCCCA GTGGACATA             150

CCAGCTGCTG TATGCCTACC CGCGGGAGAA GCCCCGTGCT TGCCCCCTGA            200

GTTCCCAGAG CATGCCCCAC TTTGGAACCC GATACGTGTG CCAGTTTCCA            250

GACCAGGAGG AAGTGCGTCT CTTCTTTCCG CTGCACCTCT GGGTGAAGAA            300

TGTGTTCCTA AACCAGACTC GGACTCAGCG AGTCCTCTTT GTGGACAGTG            350

TAGGCCTGCC GGCTCCCCCC AGTATCATCA AGGCCATGGG TGGGAGCCAG            400

CCAGGGGAAC TTCAGATCGT GATAATAAGC GGATGAATGG C                    441

( 2 ) INFORMATION FOR SEQ ID NO:26:

( i ) SEQUENCE CHARACTERISTICS:
        ( A ) LENGTH: 109 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 26:

```
GCCATTCATC  CGCTTATTAT  CACGATCCCC  CAGGTGGACG  ATGGGGGCTG         50

AGACACTGAT  GTGCCCGCAC  TCCAATGCAC  GCGTCCAGTG  ATTTTTTCT         100

CCATCTCCC                                                          109
```

( 2 ) INFORMATION FOR SEQ ID NO:27:

( i ) SEQUENCE CHARACTERISTICS:
        ( A ) LENGTH: 441 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 27:

```
GCCATTCATC  CGCTTATTAT  CACGATCTGA  AGTTCCCTG   GCTGGCTCCC         50

ACCCATGGCC  TTGATGATAC  TGGGGGGAGC  CGGCAGGCCT  ACACTGTCCA        100

CAAAGAGGAC  TCGCTGAGTC  CGAGTCTGGT  TTAGGAACAC  ATTCTTCACC        150

CAGAGGTGCA  GCGGAAAGAA  GAGACGCACT  TCCTCCTGGT  CTGGAAACTG        200

GCACACGTAT  CGGGTTCCAA  AGTGGGCAT   GCTCTGGGAA  CTCAGGGGGC        250

AAGCACGGGG  CTTCTCCCGC  GGGTAGGCAT  ACAGCAGCTG  GTATGTCCCA        300

CTGGGCGCTG  CCTCTTCCTC  ATCCCAGAAG  CAAGTGAGGT  CCTCAAATGT        350

TCGGAGAAA   CACTTCAGGG  GCTCTGAGTC  TGATGCCAGC  AAGGAGACAT        400

CTTGCGATGC  ACGCGTCCAG  TGATTTTTTT  CTCCATCTCC  C                 441
```